United States Patent [19]

Scarton et al.

[11] Patent Number: 5,804,707
[45] Date of Patent: *Sep. 8, 1998

[54] DYNAMIC HARDNESS TESTING USING MEASUREMENT OF THE SCARTON DYNAMIC HARDNESS (SDH)

[75] Inventors: Henry A. Scarton; Yau-Shing Lee; Peter A. Giacobbe, all of Troy, N.Y.

[73] Assignee: Rensselaer Polytechnic Institute, Troy, N.Y.

[ * ] Notice: The term of this patent shall not extend beyond the expiration date of Pat. No. 5,537,862.

[21] Appl. No.: 388,493

[22] Filed: Feb. 14, 1995

Related U.S. Application Data

[63] Continuation-in-part of Ser. No. 957,833, Oct. 5, 1992, Pat. No. 5,423,241.

[51] Int. Cl.$^6$ .................................................. G01N 3/30
[52] U.S. Cl. .................................................. 73/82
[58] Field of Search ........................... 73/78, 79, 81, 73/82, 579, 12.01, 12.02, 12.14

[56] References Cited

U.S. PATENT DOCUMENTS

| 465,505 | 12/1891 | Weser . | |
|---|---|---|---|
| 4,080,863 | 3/1978 | Groeschel | 84/1.27 |
| 5,079,728 | 1/1992 | Adams et al. | 364/556 |
| 5,285,687 | 2/1994 | Ringel et al. | 73/12.14 |
| 5,365,457 | 11/1994 | Madigosky | 73/573 |
| 5,537,862 | 7/1996 | Scarton et al. | 73/78 |
| 5,691,473 | 11/1997 | Peleg | 73/579 |

*Primary Examiner*—Robert Raevis
*Attorney, Agent, or Firm*—Fish & Richardson P.C.

[57] ABSTRACT

A method and apparatus for determining the degree of dynamic hardness of a material, such as a sporting equipment item. The method includes the steps of impulsively exciting a surface of the material by impacting the surface against a second, relatively hard surface in contact with a force-measuring device, and then measuring a signal from the force-measuring device to determine a frequency-dependent spectrum of the force exerted by the excited surface on the second surface. From this data, a roll-off frequency is measured and then analyzed to determine the degree of dynamic hardness of the material.

24 Claims, 15 Drawing Sheets

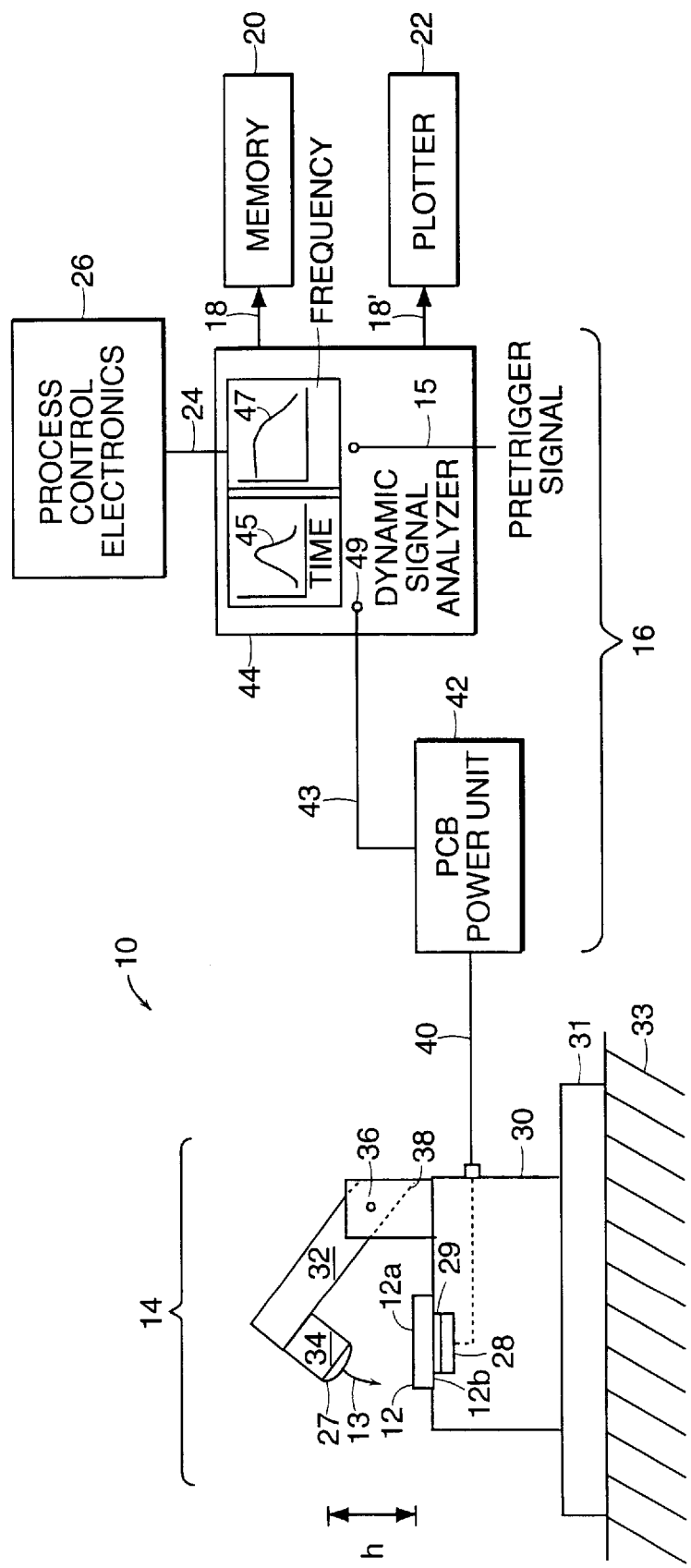
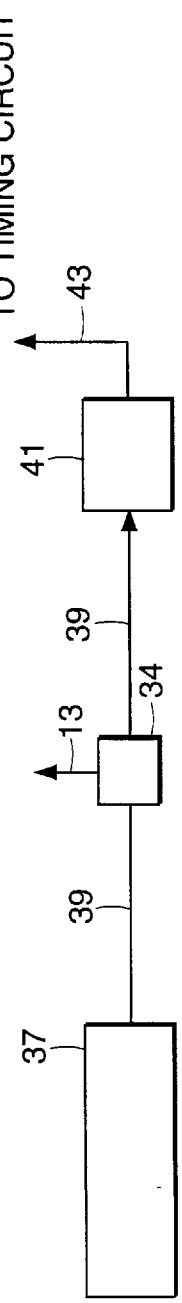
FIG. 3A
FIG. 3B

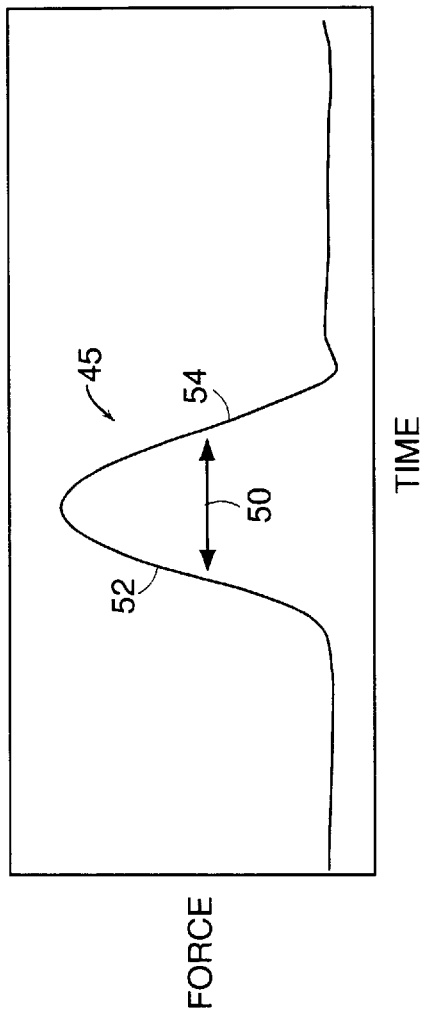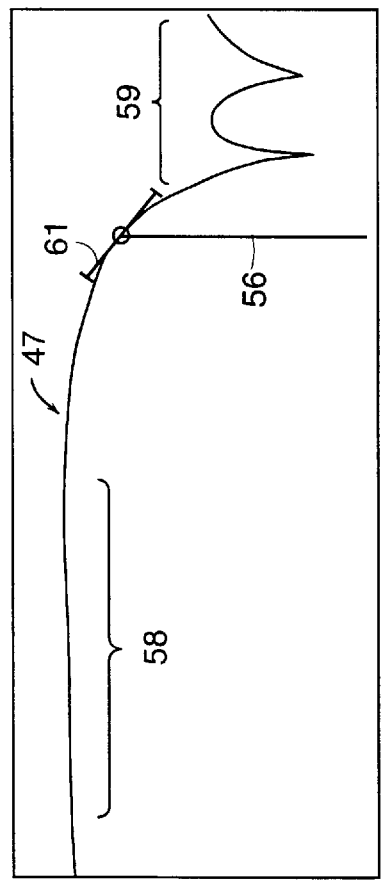

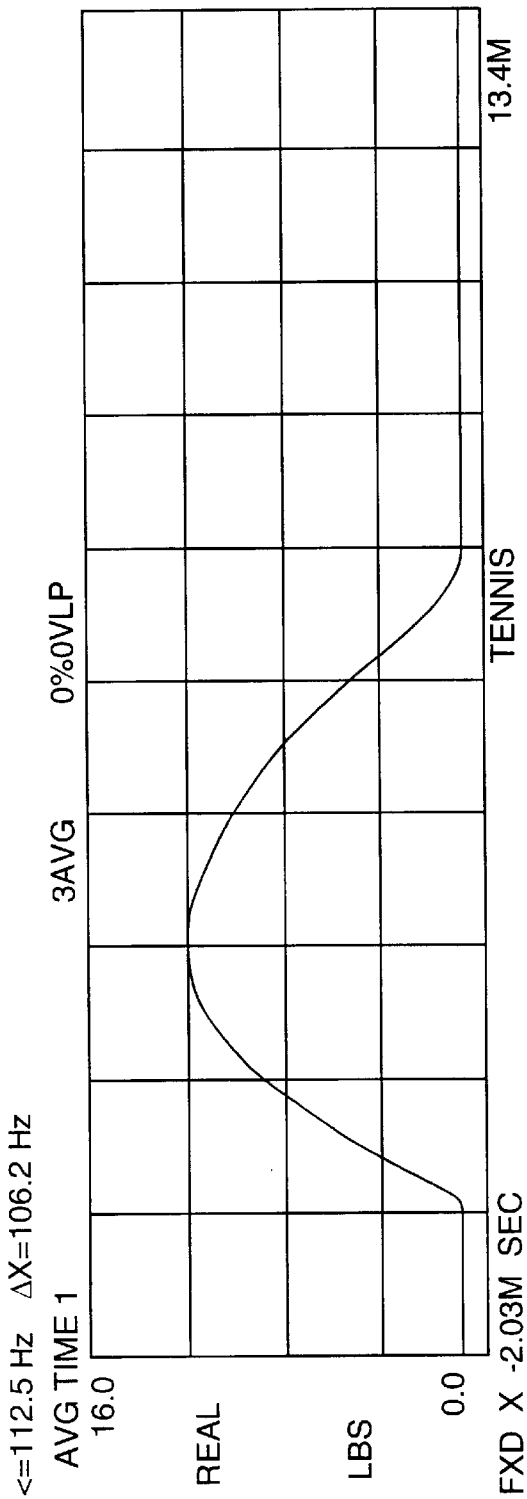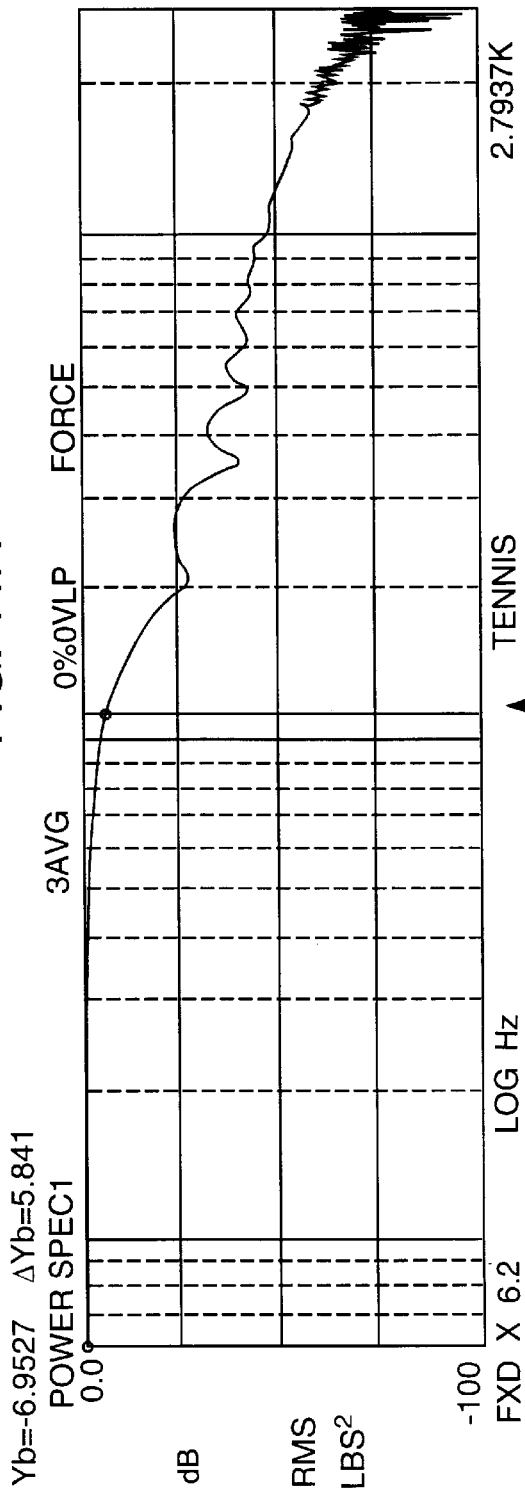

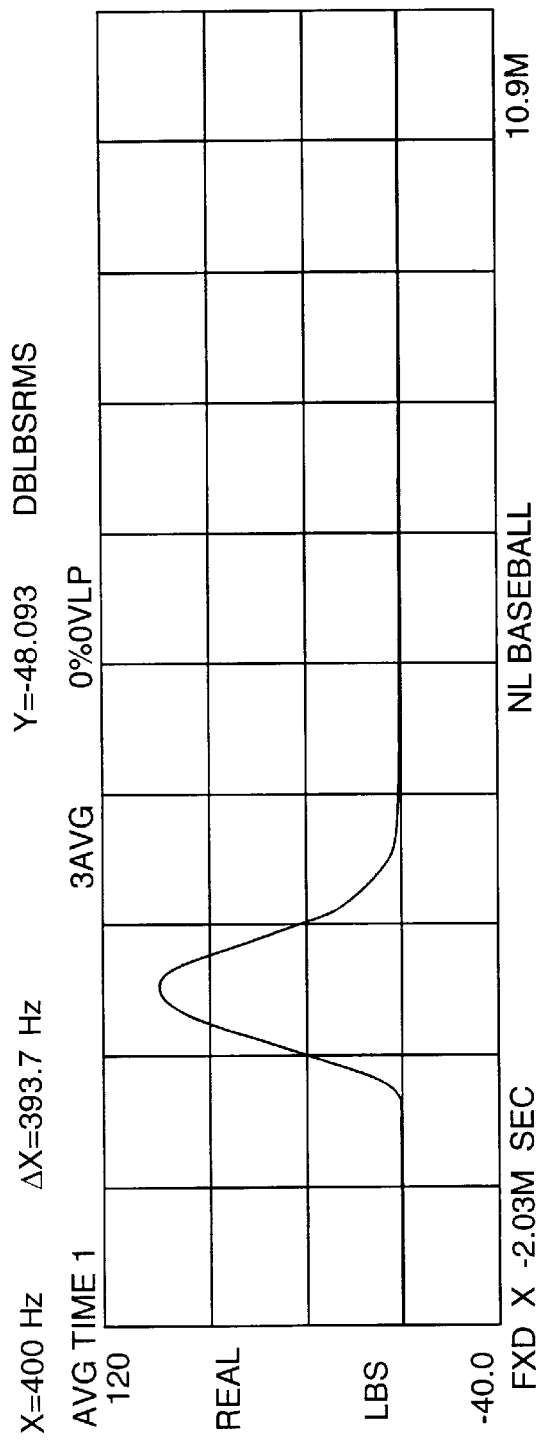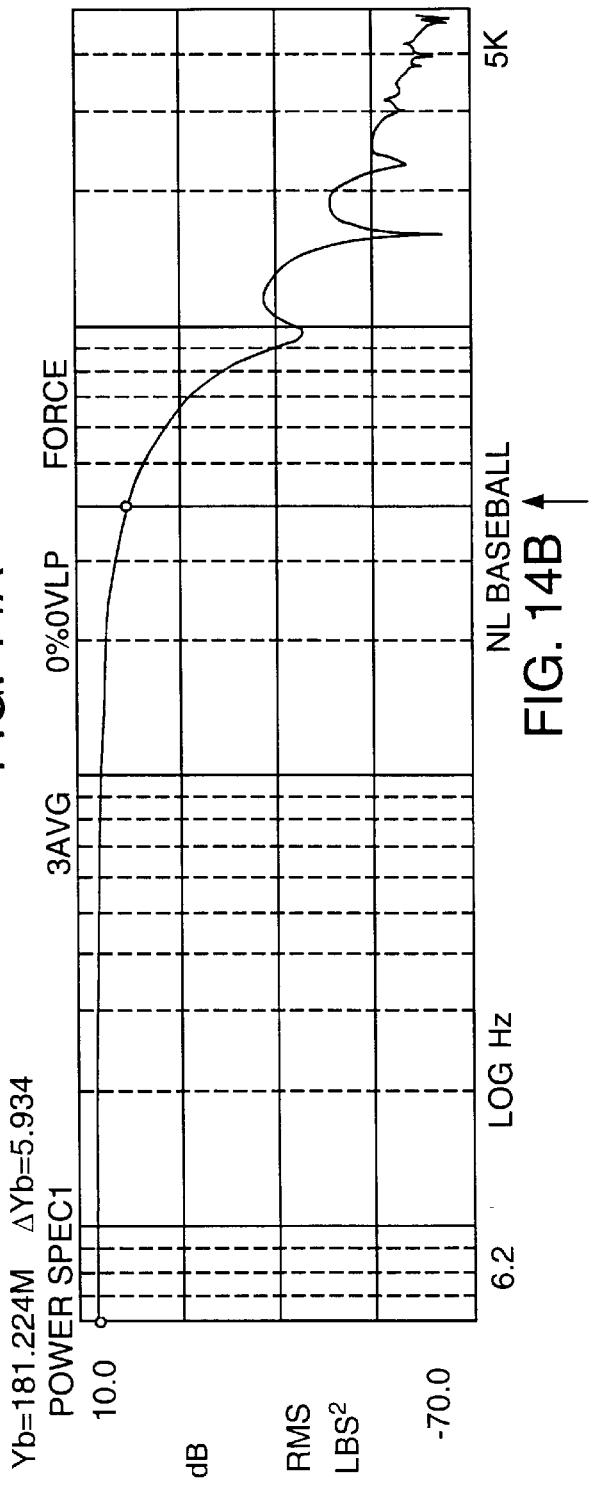

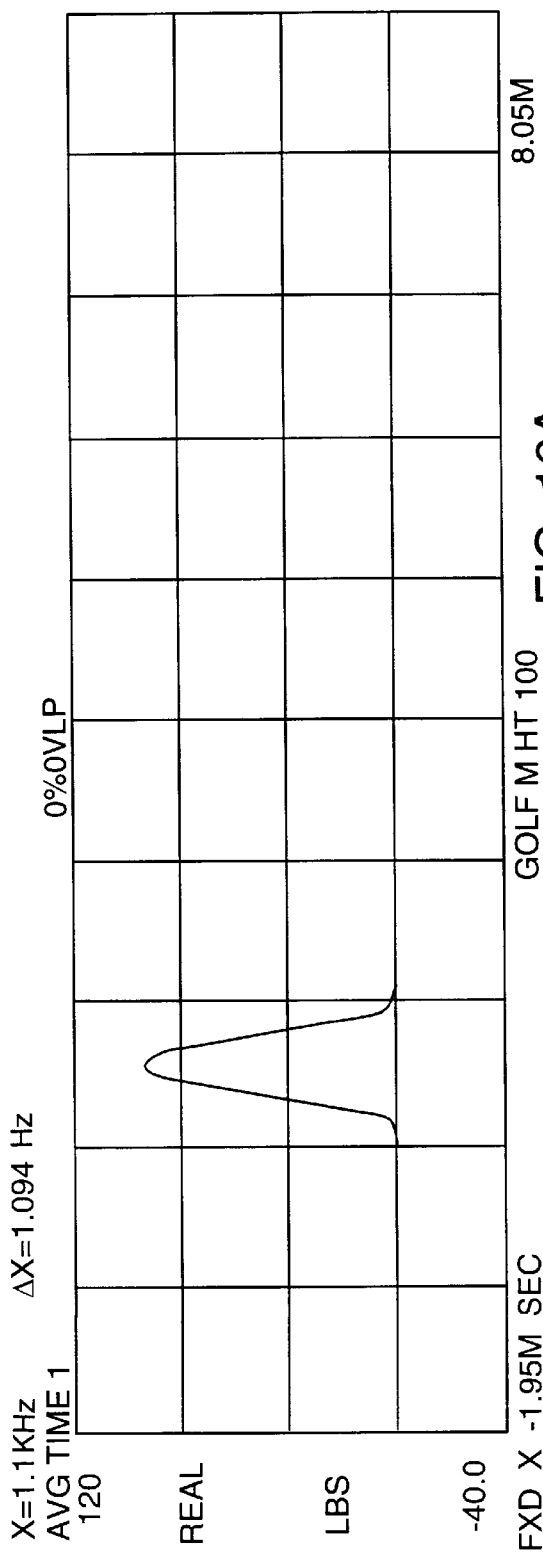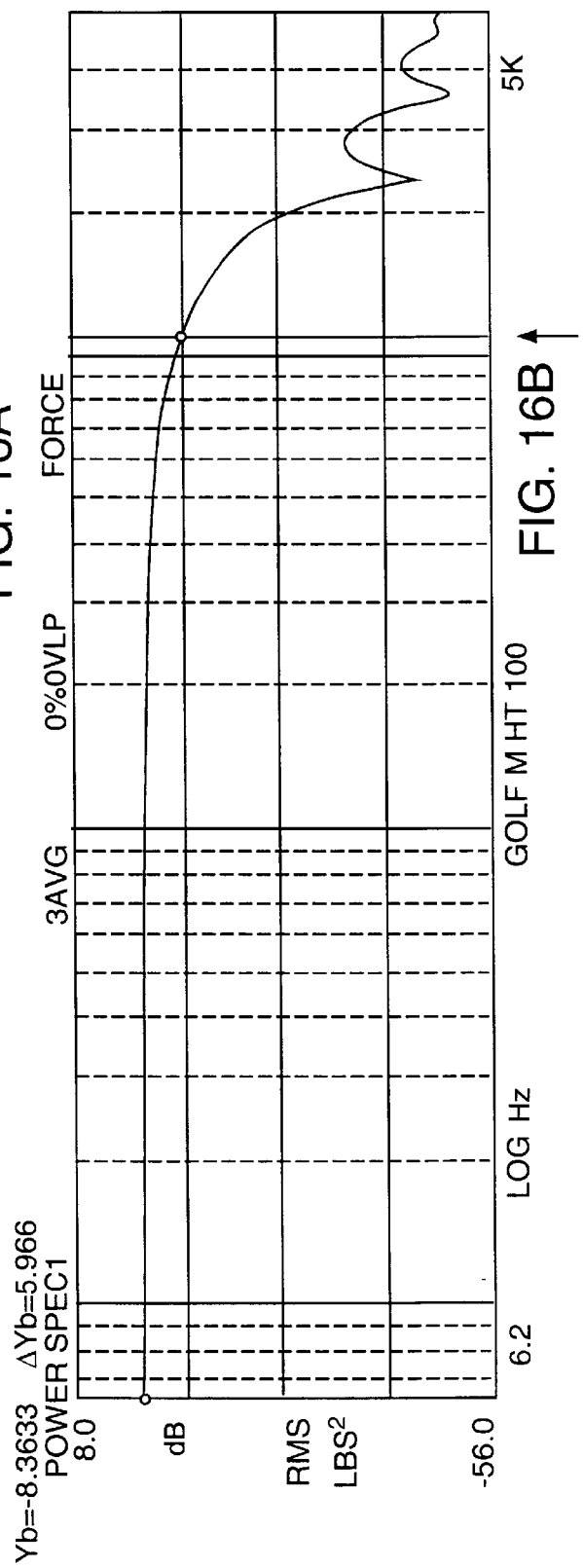

DYNAMIC HARDNESS TESTING USING MEASUREMENT OF THE SCARTON DYNAMIC HARDNESS (SDH)

This application is a continuation-in-part of U.S. Ser. No. 07/957,883, entitled "A Quantitative Method for Evaluation of the State of Piano Hammer Felt Tonal Regulation", filed Oct. 5, 1992, now U.S. Pat. No. 5,423,241.

BACKGROUND

This invention relates to methods and devices for determining the hardness of a material, particularly materials having high elastic moduli.

The term 'hardness', although inherently ambiguous, is generally defined as the ability of one body to resist penetration by another body. Alternatively, hardness has been defined as the ability of a body to resist permanent deformation. These definitions, however, do not apply to soft or elastic materials, such as rubber or other polymers, which have relatively low elastic moduli and exhibit relatively large deformations in response to pressure. These materials resist permanent deformation and are hard to penetrate. Application of the above definitions of hardness would erroneously imply that rubber is 'harder' than metallic materials, which have large elastic moduli, but relatively small ranges of elastic deformation, and are thus easy to penetrate.

Several current methods are capable of characterizing the hardness of a material, and are sensitive to plastic (i.e., inelastic), rather than elastic, material properties. Scratch hardness, often known as the Moh's scratch hardness, is the oldest form of hardness measurement. The basic principle relied on here is the ability of one material to resist being scratched by another. Diamond, for example, has the highest rating (10) on the Moh's scale, while talc has the lowest rating (1). Alternatively, the Bierbaum standard instrument, consisting essentially of a diamond point under a well-defined load, may be used to measure scratch hardness. During measurement, the point is drawn across a polished surface of the test specimen; hardness is determined by measuring the width and depth of the resulting scratch.

Static-indentation hardness testing is currently the most widely used method for determining hardness. In general, this method involves the formation of a permanent indentation on the surface of the test material; a force is required to produce the indentation, and the corresponding size, area, and depth determine the hardness value. For example, in the Brinell hardness tester, a load typically in the range of 50 to 300N is applied for 10 to 30 seconds to a hardened steel ball on the surface of the test specimen. The dimension of the indentation is measured, and the hardness is determined by dividing the applied load by the surface area of the impression, resulting in a figure-of-merit known as the Brinell hardness number (HB).

In another instrument, the Rockwell Hardness Tester, a test specimen is initially placed in contact with a preliminary load (i.e., a minor load between about 0.3 and 1N); a larger load (i.e, the major load between about 1.5 and 15N) is then applied for a specific time interval, and removed to leave the minor load. This holds the indenter at the deepest penetration, but allows elastic recovery of the material, and factors out any deformation caused by the testing apparatus. Similar indention hardness testers, based on the principle of micro-indention, can apply much smaller forces (i.e., in the range of 0.0001–100N) to produce indentations which can then be measured microscopically. Well-known devices in this area include the Knoop and Vicker's hardness testers.

For testing the hardness of elastic materials, the above-mentioned devices must produce inelastic deformations, and are incapable of providing valid measurements. This is because permanent deformation in materials such as rubber or plastic requires large amounts of indentation, and the transition point where permanent deformation occurs (i.e., failure of the elastic surface) is difficult to measure. The hardness for elastic materials, therefore, is typically defined as the resistance to elastic, rather than plastic, deformation.

The Shore Durometer measures the hardness of elastic materials over a wide range (i.e., a factor of about 200) using a compressor-pin indenter and a beam-type weighing scale. As the indenter is pressed against the surface of the test specimen, the beam compresses a resistor spring of known spring constant, and the depth of penetration is measured; in softer materials, the indentor travels deeper. The resulting figure-of-merit, the Shore Durometer hardness number, depends on the indentor's depth of penetration.

In related methods, dynamic hardness is measured by deforming or penetrating the test specimen with an indenter moving in a time-dependent, impulsive manner. In the Shore Scleroscope, for example, a dynamic load may be applied to a sample by dropping the indenter onto the test material. In this case, the hardness is expressed in terms of the impact energy and the size of the indentation.

Coefficient of restitution (COR) testing, another dynamic hardness measurement, is typically used to test the characteristics of sports balls. In this measurement technique, a ball moving at high velocities is projected onto and bounced off of a rigid surface; the ratio of the velocities after and before incidence determines the COR.

SUMMARY

In general, in one aspect, the invention provides a method for determining the degree of dynamic hardness of a material. The method includes the steps of (1) impulsively exciting a surface of the material by impacting the surface against a second, relatively hard surface in contact with a force-measuring device; (2) measuring a signal from the force-measuring device to determine a frequency-dependent spectrum of the force exerted by the excited surface on the second surface during a time period wherein the surfaces are in direct contact; (3) determining a roll-off frequency of the frequency-dependent spectrum; and, (4) analyzing the roll-off frequency to determine the degree of hardness of the material.

By "roll-off frequency" is meant a frequency which corresponds to a region of the frequency-dependent spectrum having an intensity attenuated from the maximum amplitude value of the spectrum by a predetermined amount which is preferably between 2 dB and 8 dB, and is most preferably about 6 dB.

In preferred embodiments, prior to step (2), the method further includes the step of measuring the time dependence of the force exerted by the impulsively excited surface on the second surface. Preferably, the measured time-dependent force is then processed with a Fourier transforming algorithm to generate the frequency-dependent spectrum (e.g., a power spectrum).

In other embodiments, the analyzing step further includes the step of comparing the determined roll-off frequency against a predetermined range of roll-off frequencies taken from frequency-dependent spectra of materials having known hardnesses; in this manner, the hardness of the material can be quantitatively determined. In still other embodiments, the method further includes the steps of establishing a predetermined range of acceptable impact velocities; measuring the relative impact velocity of the impacting device at the material surface; and, considering only data for instances when the measured impact velocity is within the predetermined range when determining the roll-off frequency of the frequency-dependent spectrum for the material.

Preferably, the method is used to measure a material which includes metals, ceramics, plastics, glasses, or polymers. The material, for instance, may be a sporting equipment item.

In other aspects, the invention features a method for determining the vibratory response of a material, and a method for determining the performance of a sporting equipment item. Each of these methods includes the steps of measuring the dynamic hardness of the sample (e.g., a sports ball) by impulsively exciting one of its surfaces by impacting the surface against a second, relatively hard surface in contact with a force-measuring device. This device generates a signal, which is then measured to determine a frequency-dependent spectrum of the exerted force. A roll-off frequency of the frequency-dependent spectrum is then determined and compared to a resonance frequency of the sample to determine the vibratory response.

In order to determine the performance of the sporting equipment item, the vibratory response is evaluated. In this case, during the comparing step, a relatively low roll-off frequency with respect to the sample's resonance frequency indicates that the sample will exhibit a reduced vibratory response following an impacting event. In this embodiment, the sporting equipment item is preferably a golf club or a baseball bat; the performance of other sporting equipment items may also be determined using this method.

In another aspect, the invention provides an apparatus for determining the degree of dynamic hardness of a material. The apparatus features means for impulsively exciting a surface of the material by impacting the surface against a second, relatively hard surface. A force-measuring device, in contact with the second surface, is used for generating a time-dependent signal indicating the force exerted by the excited surface on the second surface during a time period wherein the surfaces are in direct contact. A force-registering device is in electrical contact with the force-measuring device, and includes means for converting the time-dependent signal into a frequency-dependent spectrum. The apparatus also includes means for analyzing the frequency-dependent spectrum to determine a roll-off frequency; this frequency indicates the degree of dynamic hardness of the material.

In preferred embodiments, the force-measuring device is a load cell, a transducer, a strain gauge, a quartz crystal, or a piezoelectric-based device, and the force-registering device is a digital storage device (e.g., an oscilloscope). The means for converting the time-dependent signal into a frequency-dependent spectrum is preferably a Fourier transforming algorithm, and the means for analyzing the frequency-dependent spectrum is a computer program. Preferably, the relatively hard second surface is a metal plate which is contoured to match a shape of the surface of the material.

In another aspect, the invention provides an item designed to have a resonance frequency greater than its −6 dB roll-off frequency. In one embodiment, the item preferably has a spherical shape, and may be, for example, a sports ball (e.g., a golf or baseball). In another embodiment, the item comprises an elongated, substantially cylindrical or rectangular portion, and may be, for example, a baseball bat, hockey stick, or a golf club. In an alternate embodiment, the item is designed to have a resonance frequency less than its −6 dB roll-off frequency. Here, the item may be an reduced-injury-factor (RIF) sports ball, or a set of racket strings.

In another embodiment, the item is designed so that the magnitude of the SDH-DSDH product of the item is greater than $\gamma$, where $\gamma=0.7737$; this allows negative damping (i.e., "trampoline" or acoustic effects, described in detail below) of the item to be enhanced. Alternatively, in order to reduce the elastic properties of the item, it may be designed so that the SDH-DSDH product of the item is less than $\gamma$. In these cases, "item" is meant any of the items of sports equipment described below, or any portion of these items.

The inventions have many advantages. In general, the method and apparatus allow for dynamic, non-destructive evaluation of a material's dynamic hardness, as compared to conventional methods based on static measurements. This allows return of the elastic (i.e., compliance-related) properties of the test material, whereas most current tests are dependent on a combination of plastic and elastic material properties. In addition, when compared to COR measurements, the method is simple and easy to perform, and does not damage the sample in any way. The method, therefore, allows accurate and repeatable determination of the dynamic hardness of elastic materials, such as those used in sports equipment. The measurement can be performed in a number of different ways; in all cases, once a standard testing procedure is established (e.g., a standard impact velocity and experimental geometry), the properties of the sample are independent of the method used to determine them. Thus, the measured property can be used universally to classify the sample for a given standard condition.

Moreover, the method provides a quantitative means for measuring inertial as well as stiffness characteristics. The method may be used, for example, as a process-control measure during the manufacturing of a wide variety of sports items, including, among others, baseballs, softballs, golf, ping pong, racquet, bowling, and tennis balls, hockey pucks, marbles, bowling pins, gloves, rackets, shin guards, and paddles. When implemented into the ball-manufacturing process, the method allows the dynamic hardness of each ball to be accurately measured; samples having dynamic hardness values lying outside a well-defined range can be singled out during manufacture.

These and other features and advantages of the invention will be seen from the following description of the presently preferred embodiments, and from the claims.

BRIEF DESCRIPTION OF THE DRAWINGS

FIG. 3A is a somewhat schematic representation of a dynamic hardness tester and associated detection electronics according to one embodiment of the invention;

FIG. 3B is a schematic diagram of the timing apparatus used with the dynamic hardness tester shown in FIG. 3A;

FIGS. 4A and 4B are generic plots showing, respectively, the time-dependent force-versus-time material response following impulsive excitation, and the power spectrum of the time-dependent material response;

FIGS. 11A, 12A, 13A, 14A, 15A, and 16A are plots of the time-domain material responses taken from, respectively, tennis ball, racquet ball, softball, baseball, hockey puck, and golf ball samples following impulsive excitation; and FIGS. 11B, 12B, 13B, 14B, 15B, and 16B are plots of the power spectra of the data shown in, respectively, FIGS. 1A, 12A, 13A, 14A, 15A, and 16A.

DETAILED DESCRIPTION

The invention provides a method for measuring the frequency-dependent response (e.g., the power spectrum) of a sample in order to determine its dynamic hardness. The method is particularly effective for determining the dynamic hardness of elastic samples, such as sports balls. Referring first to FIGS. 1A–1C, and 2A–2C, the time-dependent response of a sports ball to an impulsive, impacting force is directly related to the ball's dynamic hardness. For example, when struck with the head 4 of a golf club, a golf ball 2 having a low mass (typically about 45 grams) and a high stiffness undergoes a small degree of deformation, indicated in FIG. 1B by a "flattening" of the impacted surface 5. During impact, the club head 4 and the ball 2 are in contact for a short time period (a few hundred microseconds), during which the ball exerts an opposing force on the club head. Following this contact period, the ball is elastically propelled, and the force exerted by the ball is terminated.

Figure 1A:
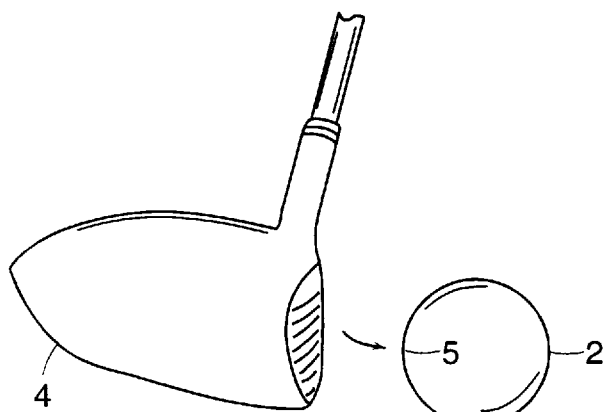
FIGS. 1A–1C are perspective views showing, respectively, a golf ball prior to impact with a club head, during impact, and following impact.
Figure 2A:
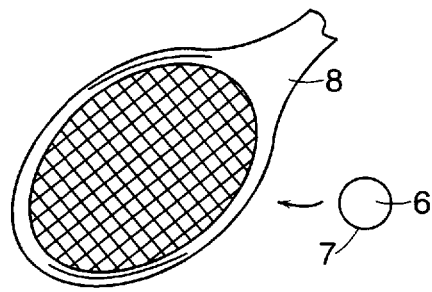
FIG. 2A–2C are perspective views showing, respectively, a tennis ball prior to impact with a racket, during impact, and following impact.
Figure 1B:
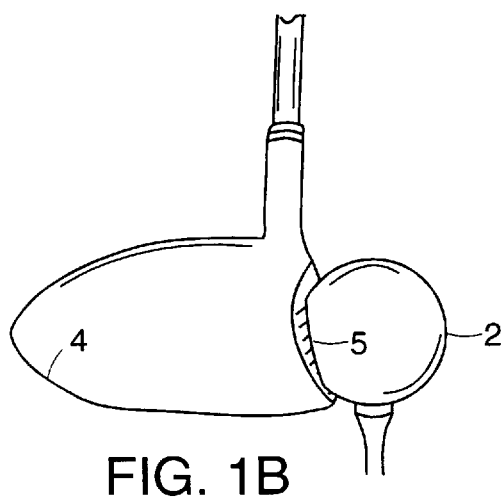
Figure 2B:
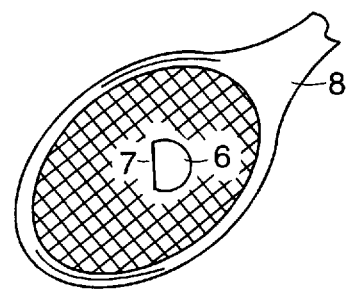
Figure 1C:
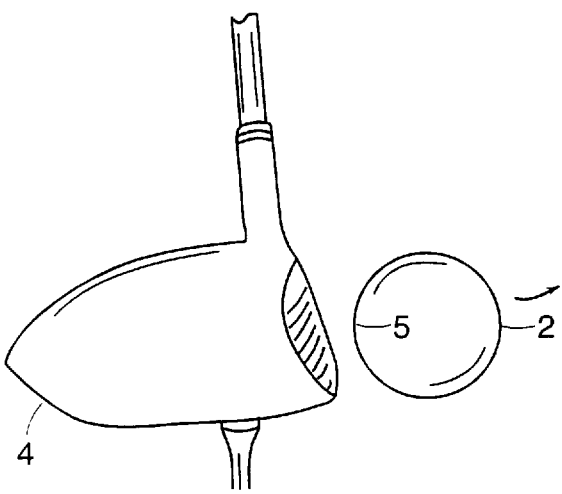
Figure 2C:
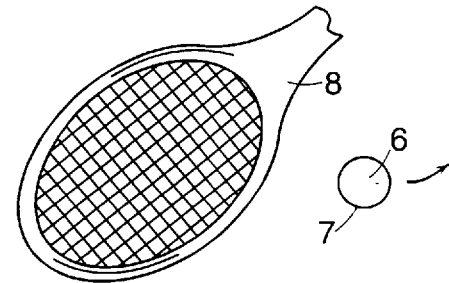
Figure 5A:
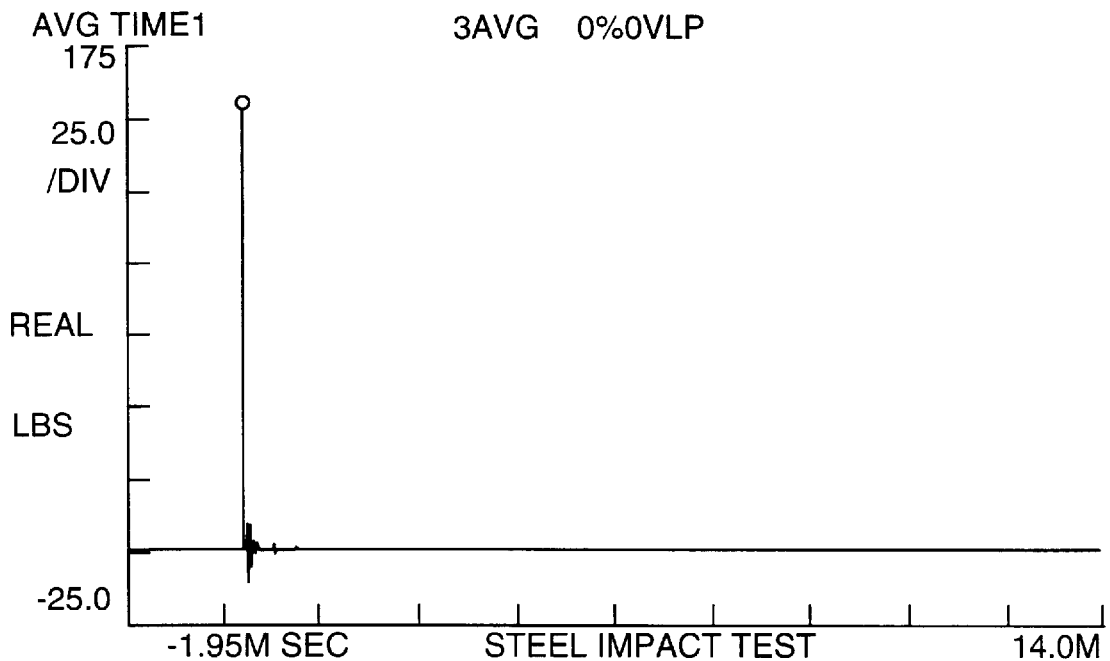
FIGS. 5A, 6A, and 7A are plots of the time-domain material responses taken from, respectively, steel, aluminum, and rubber samples following impulsive excitation.
Figure 5B:
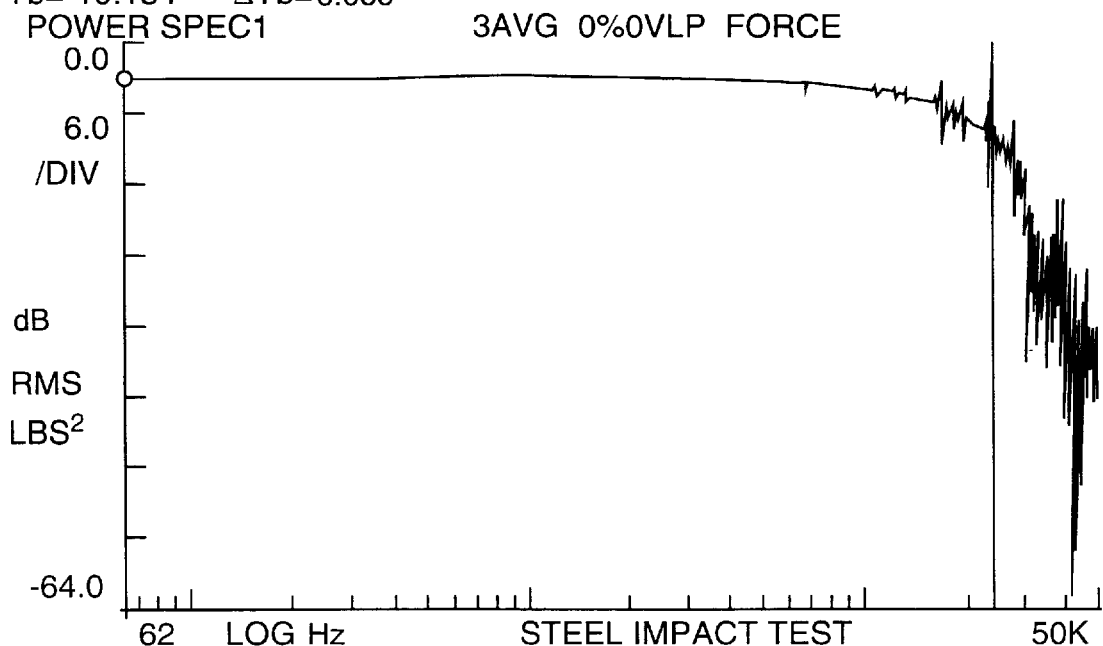
FIGS. 5B, 6B, and 7B are plots of the power spectra of the data shown in, respectively, FIGS. 5A, 6A, and 7A.
Figures 6A, 6B:
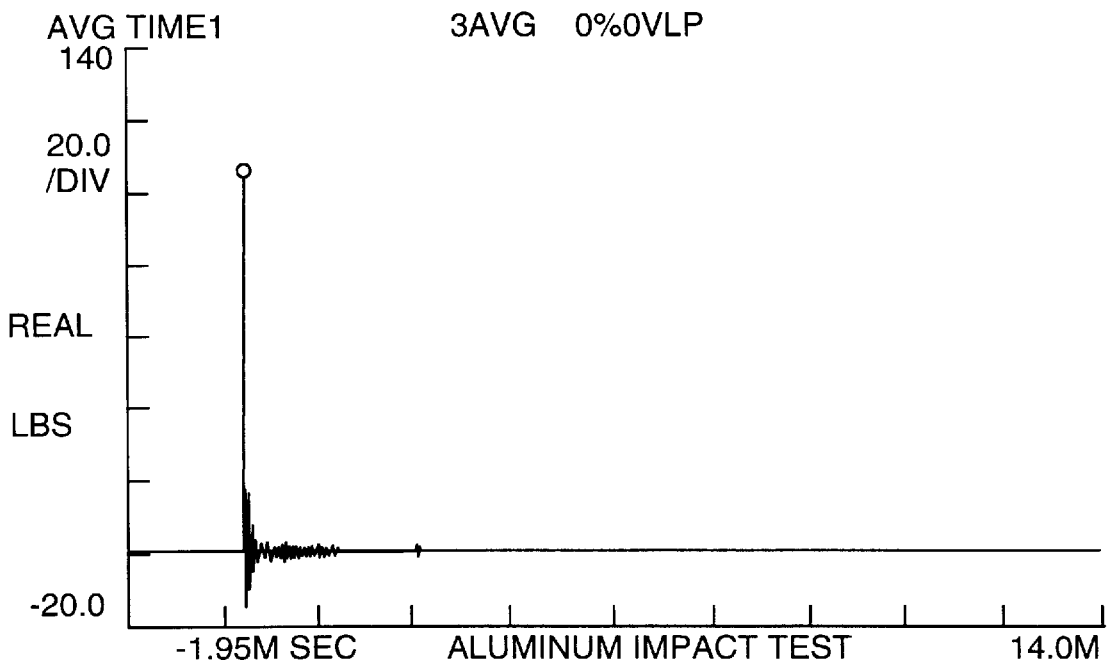
Figure 7A:
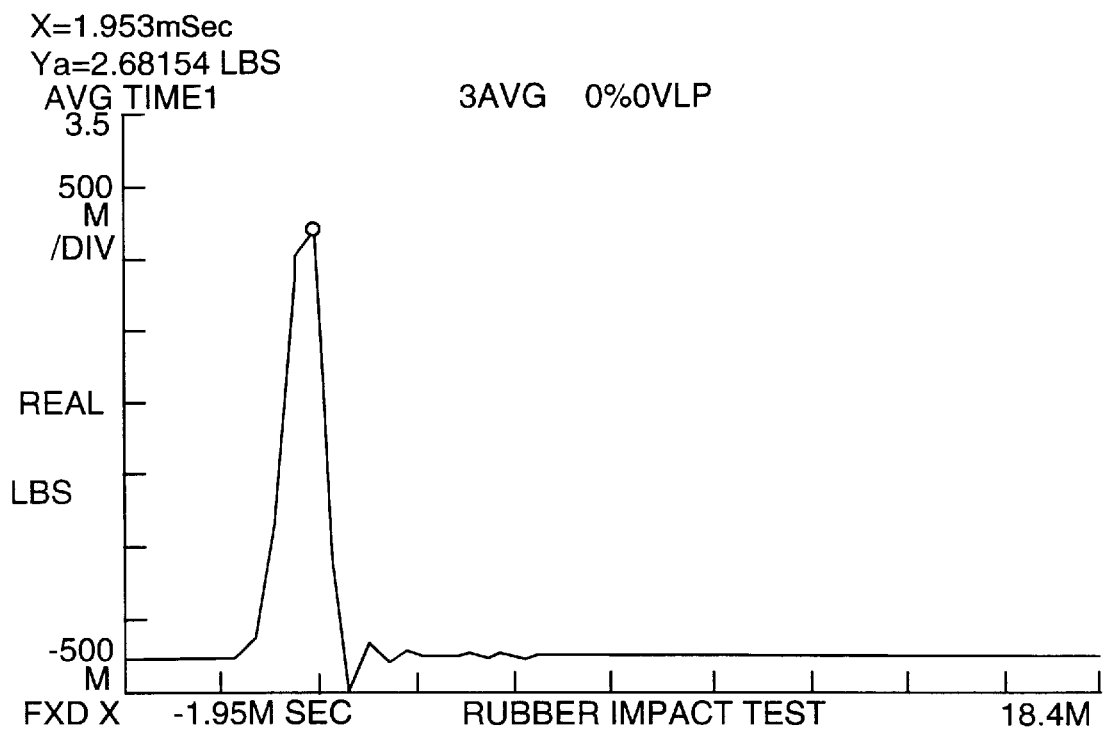
Figure 7B:
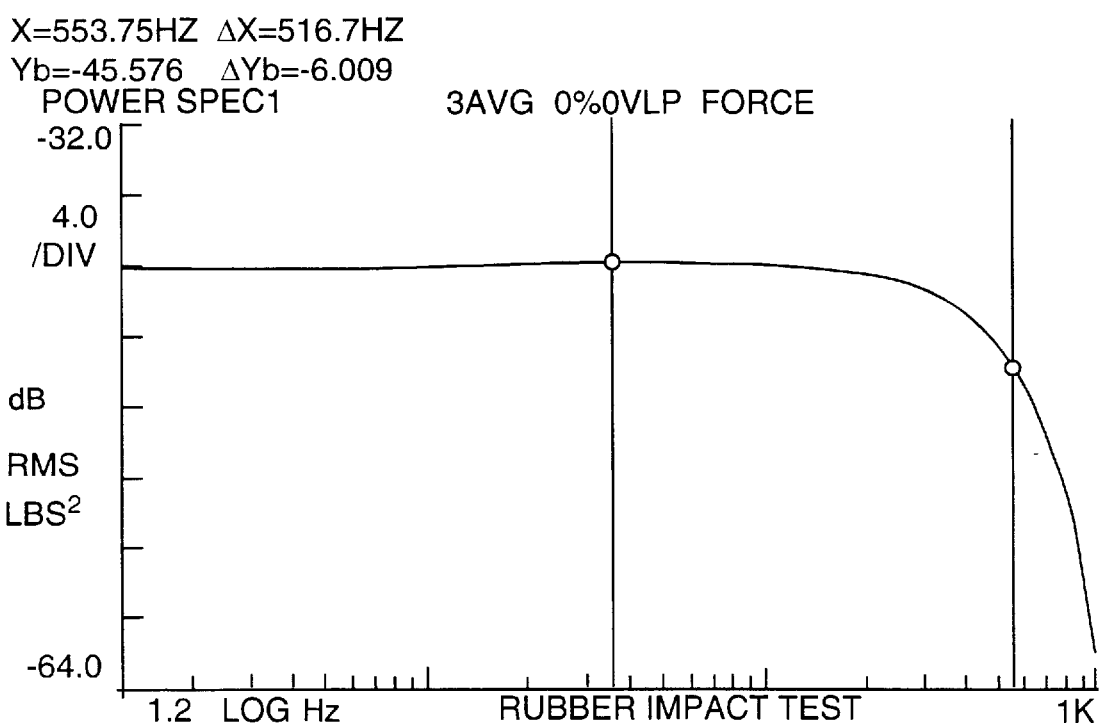

In contrast, as shown in FIG. 2B, a tennis ball 6 having a similar mass (about 57 grams) but lower stiffness compared to the golf ball flattens along an impacted surface 7 by a relatively large amount when struck with the face 8 of a tennis racket. In this case, during impact, the ball 6 is in contact with the racket face for a relatively long period of time (a few milliseconds), during which an opposing force is exerted. Thus, in both cases, the ball's time-dependent response to an impulsive force is directly related to its dynamic hardness: samples with high stiffness/mass ratios, such as golf balls, have fast temporal responses and are 'harder' than samples with relatively lower stiffness/mass ratios, such as tennis balls, which exhibit slower temporal responses.

During an actual measurement process, the sample's time-dependent response is first determined using the apparatus described in detail below, and then Fourier transformed to generate the power spectrum of the time-dependent material response. These data are then analyzed to determine a "roll-off" frequency corresponding to a region of the power spectrum having an intensity attenuated from the spectrum peak by a predetermined amount (e.g., −6 dB). The roll-off frequency is directly related to the square root of the stiffness-to-mass ratio, and can be used to quantitatively determine the sample's dynamic hardness.

The apparatus used to generate and measure the sample response impulsively excites the sample with a force-delivering mechanism, and then measures the time-dependent force exerted by the sample on a force-sensitive device.

Referring now to FIG. 3A, in one embodiment, a dynamic hardness tester 10 used to monitor the dynamic hardness of a sample 12 includes a force-delivering mechanism 14 for impulsively exciting the sample 12, and a force-registering mechanism 16 for detecting the material response. Once detected, an output signal from the force-registering mechanism 16 can be sent along signal lines 18, 18' for, respectively, input to a plotter 22 or a computer memory 20, such as a computer disk drive. Alternatively, the output signal may be sent along a signal line 24 to a series of process control electronics 26 capable of analyzing the signal to gauge the dynamic hardness of the sample 12. This allows, for example, evaluation of the dynamic hardnesses of materials being processed in an assembly line.

During the measurement process, the force-delivering mechanism 14 imparts an impulsive force on the sample 12. A force-sensitive load cell 28 capable of measuring an axial force is mounted in a large block 30, representing an effectively infinite mass. The load cell includes an impacting plate 29 in direct contact with the sample 12; this plate must be harder than the sample being impacted, and may be conformed so that its shape is matched to the surface of the sample. In general, the load cell 28 may be any sensor which, in the presence of an axially applied force, can measure a load. Preferably, the load cell is optimized to measure a dynamic load, and has a relatively constant frequency response from less than 100 Hz to greater than about 50 kHz. For example, the load cell may be a quartz crystal or similar piezoelectric or transducer-based device, or a strain gauge.

During operation, the sample 12 may be placed on top of the impact plate 29 and the load cell 28, and beneath an impacting device, such as a axially rotating hammer 32 including an impacting head 34 with a tip 27. The tip preferably has a radius of curvature (shown here as R) to ensure that an evenly distributed force is delivered to the sample. In this case, the hammer 32 is elevated above the sample using an arm 38, and rotates about a pivot point 36 along a path indicated by the arrow 13. The magnitude of the force delivered by the hammer 32 to the sample 12 is directly related to a height h of elevation relative to the surface of the sample.

In order to generate the time-domain signal, the relatively hard hammer tip 27 impacts the relatively soft upper surface 12a of the sample 12. The contact time between the tip 27 and the samplers upper surface 12a is directly related to the sample's dynamic hardness. As described above, during contact, the hammer tip exerts a force on the sample, which, in turn, passes through the sample and is detected by the load cell attached to the heavy mass; this allows generation of a time-dependent response which is sent along the signal line 40 to the force-registering mechanism 16. In order to damp out any vibratory motions not related to the material response, the infinite-mass block 30 is preferably mounted on a vibration-isolating pad 31 in contact with a ground surface 33.

A power unit 42 and dynamic signal analyzer 44 contained within the force-registering mechanism 16 are used to analyze and process the detected signal. In certain embodiments, the power unit provides a DC voltage (typically around 5 volts) to the load cell 28, and is capable of receiving a time-dependent signal. Once received, the signal is sent along a signal line 43 to an input channel 49 of a dynamic signal analyzer 44. This device may be, for example, a transient digitizing or storage oscilloscope having a suitable bandwidth for time-resolving and digitizing the output from the power unit 42. Preferably, this device has Fourier transforming and signal averaging capabilities, thereby allowing multiple time-domain waveforms 45 to be averaged together and then converted into a frequency-domain spectrum 47. As described above, following processing, the signal corresponding to the spectrum data points is sent along signal lines 18, 18' to, respectively, the memory 20 or plotter 22 for storage or display, or, alternatively, to the series of process control electronics 26 implemented into a manufacturing line.

Timing of the measurement device 10 is necessary to synchronize and trigger the force-delivering and force-registering devices. Preferably, the dynamic signal analyzer is operated in "pretrigger" mode. In this case, prior to impact, an internal analog-to-digital converter in the dynamic signal analyzer 44 is activated so that analog signals sent along a signal line 43 may be digitized and collected in a buffer. Following impact of the sample, an electronically delayed "pretrigger" signal is sent along a signal line 15 to the dynamic signal analyzer 44 to stop the data-collection process, thereby allowing a window of data points stored in the buffer to be recorded and, if desired, displayed. In order to adjust the position of the signal displayed on the analyzer, the timing of the pretrigger signal is adjusted using, for example, electronic delay means known in the art.

In alternate embodiments, other mechanisms can be used to trigger the signal analyzer. Referring now to FIG. 3B, optical means, such as a laser light source 37, may be used to generate a timing signal which is sent along a signal line 43 to a timing circuit 51 providing a trigger input to the dynamic signal analyzer 44. In this case, an optical beam 39 generated by the laser 37 is oriented perpendicularly to path of travel 13 of the impacting head 34 of the hammer 32. The beam's position is adjusted so that it impinges an optical detector 41, such as a photodiode, capable of generating the light-induced signal. During operation, the impacting head 34 swings downward and traverses the beam path for a short time period, thereby completely blocking the beam 39 and generating a null in the light-induced signal. The signal is then sent along the signal line 43 to an input channel of the timing circuit 51, where it is processed and converted into a waveform suitable for triggering.

The time-domain signal recorded by the signal analyzing device is a function of the relative impact velocity ($v_0$) between the impacting device and the sample. This velocity can be determined for a particular test procedure, and can be held constant and used to establish uniformity during the testing procedure. For example, when the sample is impulsively excited by dropping it on the load cell (as is described in detail below), and the dropping height h is relatively low (i.e., within a few feet of the impact plate), the effects of air drag can be neglected, and the impact velocity can be determined using the formula $v_0 = (2gh)^{1/2}$ where g is the force of gravity. Similar treatment can be used when a frictionless pendulum is used as the impactor. Alternatively, $v_0$ can be determined using optical means similar to those shown in FIG. 3B. In this case, two beams similar to the beam 39 are separated by a known distance and disposed along the path 13. As the sample or impactor is falling, signals indicative of the time-dependent position are recorded by separate optical detectors (similar to detector 41) and used to calculate $v_0$.

Referring to FIG. 4A, a time-domain waveform 45, indicative of the typical response of a sample measured with the apparatus of FIGS. 3A and 3B, has a gaussian shape with the full width at half the maximum height (FWMH, indicated by the arrow 50) of the response related to the stiffness of the material. For instance, stiffer materials will have a more rapid response to the impulse function (meaning that they are in contact with the impacting tip for a shorter period of time), and thus the associated waveforms will have smaller FWMHs. In addition, for harder samples, both the rising 52 and falling 54 edges of the waveform will be steeper.

The time-domain waveform can be processed using well-known Fourier analysis techniques to generate a power spectrum waveform 47, as shown in FIG. 4B. The power spectrum may be a plot of the log of the square of the force amplitude as a function of the log of the corresponding oscillation frequencies. This log-log plot allows emphasis of the low-amplitude and low-frequency spectral components. The plot may also be presented using two linear axes. In this manner, the minimum amount of data points are required for complete specification of the material response. In other embodiments, the frequency-dependent spectrum may be a plot other than the power spectrum. For example, the spectrum may simply include the force amplitude or its real or imaginary parts as a function of frequency.

The log amplitude of the power spectrum corresponding to the time-dependent gaussian waveform 45 is generally frequency independent at low frequencies (indicated by the baseline region 58), and begins to decrease in intensity at higher frequencies. The −6 dB roll-off frequency of the power spectrum ($\omega_{-6\ dB}$, indicated in the figure by the line 56) is the frequency corresponding to the point when the waveform 47 falls to six decibels below its peak value (in this case, the value of the baseline 58). This frequency, called the "Scarton Dynamic Hardness" or SDH, can be used to gauge the dynamic hardness of a material, and can be determined in both linear and nonlinear systems. If r is defined as a force ratio taken from the power spectrum so that $$r = \frac{\text{Force}_{-6dB}}{\text{Force}_{max}} \tag{1}$$

and $$\beta(dB) = 10\log_{10}r^2 \tag{2}$$

then at −6 dB, $r^2$ is 0.25, and r=0.5. Thus, the SDH represents the point at which the force-generating mechanism excites frequencies having amplitudes which are one-half the amplitude of frequencies excited at the maximum spectral components.

The SDH, in general, gives information about how much low-frequency vibratory energy will be transmitted into an impactor (such as a bat, racket, or hockey stick) following an impulsive interaction with a sample (such as a ball or puck). This measurement allows the performance of the sample to be evaluated in a distinctive and repeatable manner. A roll-off frequency occurring at −6 dB is chosen mainly because the power spectrum amplitude at this value is measurably different from the baseline amplitude, while being separated from the spectrum noise shown in the figure as the region 59. While $\omega_{-6\ dB}$ is the preferred roll-off frequency, it is understood that other frequencies corresponding to spectral components attenuated by various degrees from the baseline amplitude, such as those occurring at −4 or −8 dB, may also be used to gauge the dynamic hardness of the material.

The slope (or derivative "D") of the power spectrum at $\omega_{-6\ dB}$, indicated in FIG. 4B by the line 61, is the "DSDH" value of the sample and relates to the degree of damping of the sample's frequency response. A power spectrum which rolls off rapidly has a DSDH value which is negative in sign and has a large amplitude; slower roll-off behavior results in a DSDH value which is still negative in sign, although the magnitude of the coefficient will be smaller. Like the SDH, the DSDH values may be determined for linear and non-linear systems. In order to extract the DSDH value from a frequency-dependent plot, it may be desirable to plot data on a log-log scale, rather than a linear scale, before determining the slope at $\omega_{-6\ dB}$; in this way, the influence of the zero-frequency point can be minimized. In preferred embodiments, both the SDH and DSDH are determined for a sample during a measurement process.

The SDH and DSDH values for materials can be derived using spring-mass model systems. In particular, $\omega_{-6\ dB}$ for a simple undamped spring-mass system (or a more complex Hooke's law-based Hertzian Contact Model, discussed below) is related to the fundamental oscillation frequency of the system $\omega_0$ (having units of radians per second):

$$\omega_{-6\ dB} = 1.639\ \omega_0 \quad (3)$$

where k is the effective spring constant of the material and $$\omega_0 = \sqrt{\frac{k}{m}} \quad (4)$$

m is the mass of the impactor. Assuming a that the impactor is spherical, has a radius $R_1$, and is relatively hard compared to the impacted material, the effective spring constant k can be calculated from the Hertz Law of Contact. Here, the force-deformation relation is $$F = bd^{3/2} \quad (5)$$

where d is the deformation of the contacting bodies, and b, for a sphere in contact with a plane surface, is $$b = \sqrt{\frac{16 R_1}{9\pi^2 (\delta_1 + \delta_2)}} \quad (6)$$

where $$\epsilon_1 = \frac{1 - \nu_1^2}{\pi E_1} \quad (7)$$

$$\epsilon_2 = \frac{1 - \nu_2^2}{\pi E_2} \quad (8)$$

and $\epsilon$ is a constant and $\nu$ and E are the Poisson's ratio, and Young's modulus for the impactor ($\epsilon_1$, $\nu_1$, $E_1$) and impacted material ($\epsilon_2$, $\nu_2$, $E_2$). For this model, the maximum deformation $d_m$ is given by $$d_m = \left( \frac{5 v_0^2}{4 A_1 b} \right)^{2/5} \quad (9)$$

-continued $$A_1 = \frac{1}{m_1} \quad (10)$$

where $v_0$ is the impact velocity.

Once $\nu$ and E are determined, other related elastic properties, such as stiffness and coefficient of restitution can be determined. In addition, the DSDH for the springmass model with no damping described above is related to $\omega_{-6db}$ by a constant:

$$DSDH = \frac{-\gamma}{\omega_{-6dB}} \quad (11)$$

where $\gamma$, as described above, equals 0.7737.

A more complex model (based on the Hertzian contact model) which can be used to estimate dynamic hardness involves a spherical impactor in contact with an infinite plane surface (i.e., the semi-infinite surface model). In this case, the two impacting bodies will be subjected to an indentation in the vicinity of the point of contact. In general, $A_1$ and b for this model are described in equations 5–10 above, and the relationship between the elastic properties of the impacted material, impactor, and roll-off frequency is obtained using:

$$\epsilon_2 = 0.247 \left( \frac{v_0 R_1 A_1^2 \pi^3}{\omega_{-6dB}^5} \right)^{1/2} - \epsilon_1 \quad (12)$$

When the impactor is assumed to be very hard relative to the soft specimen, $\epsilon_1$ becomes very small, and equation (12) becomes $$\epsilon_2 = 0.247 \left( \frac{v_0 R_1 A_1^2 \pi^3}{\omega_{-6dB}^5} \right)^{1/2} \quad (13)$$

Thus, using equation (12), the −6 dB roll-off frequency can be related to the elastic properties of the impactor and impacted material.

Equation (13), in addition, can be rearranged to show that the roll-off frequency is dependent on the impact velocity between the two materials, and to show that $$\frac{v_0}{\omega_{-6dB}^5} = \text{constant} \quad (14)$$

Thus, the SDH of a material scales with the impact velocity:

$$\omega_{-6dB,2} = \omega_{-6dB,1} \left( \frac{v_2}{v_1} \right)^{1/5} \quad (15)$$

For example, a baseball having a SDH value measured to be 400 Hz at 7.3 ft/second, when pitched at 100 miles per hour and impacted with a bat moving at 30 miles per hour, will have an effective SDH value of about 730 Hz.

Calculated and experimentally measured SDH values can be compared in order to demonstrate the accuracy of the above models. In a particular example, the experimentally determined SDH values for steel, aluminum, and rubber samples were determined by measuring the time and frequency dependent responses shown, respectively, in FIGS. 5A, 6A, 7A, and 5B, 6B, and 7B. The measured SDH values were then compared to calculated values determined using the un-damped Hooke's law model (Model 1) and the semi-infinite surface model (Model 2). The calculated SDH values the models use nominal material properties. The values of the actual material properties are unknown, and therefore result in some deviation (indicated as "% Dev." in Table 1, below) for the calculated data.

TABLE 1

Calculated and Experimentally Measured SDH Values

| Material | Measured SDR | Model 1 SDH | % Dev. | Model 2 SDH | % Dev. |
|---|---|---|---|---|---|
| Steel | 23,375.0 | 24,857.9 | 6.34 | 23,731.7 | 1.53 |
| Aluminum | 18,937.5 | 19,040.4 | 0.54 | 18,177.7 | 4.01 |
| Rubber | 553.8 | 455.4 | 17.8 | 434.7 | 21.5 |

Based on the derivations of the roll-off frequencies for Models 1 and 2, the SDH values can be calculated and compared for a variety of other metals (i.e., lead, magnesium, and copper), glasses (i.e., pyrex and quartz), plastics (i.e., polyethylene and polyimide), and soft rubber. The results of these calculations, along with the Poisson's ratio and Young's modulus for the material, are shown in Table 2, below.

TABLE 2

Calculated SDH Values for Models 1 and 2

| Material | E (Pa) | ν | Model 1 SDH | Model 2 SDH |
|---|---|---|---|---|
| Lead | $1.57 \times 10^{10}$ | 0.43 | 11,870.9 | 11,333.1 |
| Magnesium | $4.21 \times 10^{10}$ | 0.31 | 16,138.9 | 15,407.7 |
| Copper | $12.41 \times 10^{10}$ | 0.37 | 22,444.0 | 21,427.1 |
| Pyrex | $6.206 \times 10^{10}$ | 0.24 | 18,045.4 | 17,227.9 |
| Quartz | $7.170 \times 10^{10}$ | 0.16 | 18,669.4 | 17,823.6 |
| Polyethylene | $0.069 \times 10^{10}$ | 0.46 | 3,541.2 | 3,380.8 |
| Polyamide | $0.207 \times 10^{10}$ | 0.40 | 5,343.5 | 5,101.4 |
| Soft Rubber | $1.30 \times 10^{6}$ | 0.495 | 293.4 | 280.1 |

More complete derivations of the properties of these models, and the associated calculations, are described in the thesis proposal of Yau-Shing Lee entitled "Dynamic Hardness Testing", submitted confidentially to the Department of Mechanical Engineering Thesis Graduate Committee at the Rensselaer Polytechnic Institute, Troy, N.Y., 1994, the contents of which are incorporated herein by reference.

Figure 8A:
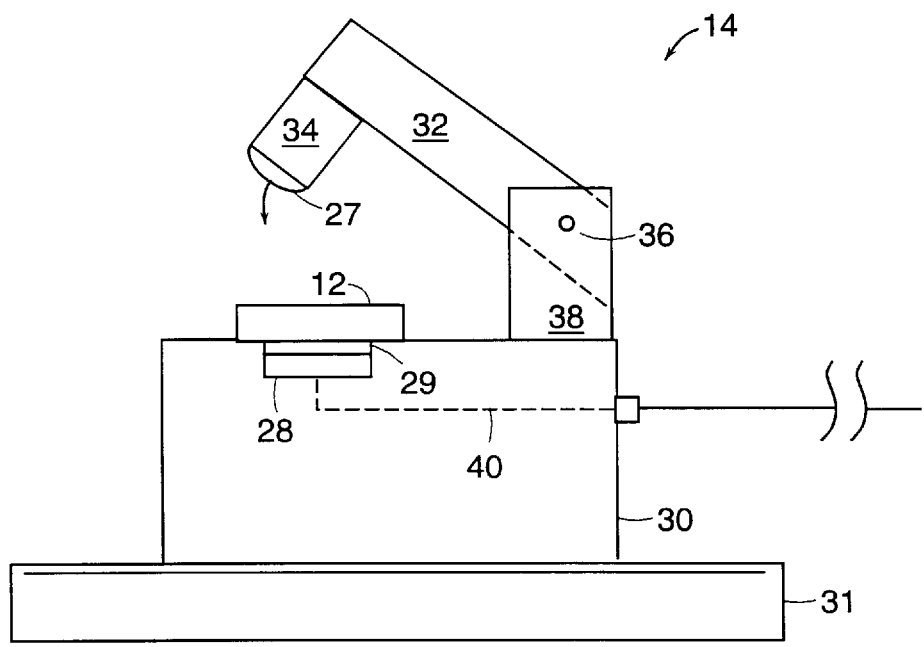
FIGS. 8A and 8B are side views of the dynamic hardness tester wherein a load cell is attached, respectively, to an inertial mass, and to a force-delivering mechanism.
Figure 8B:
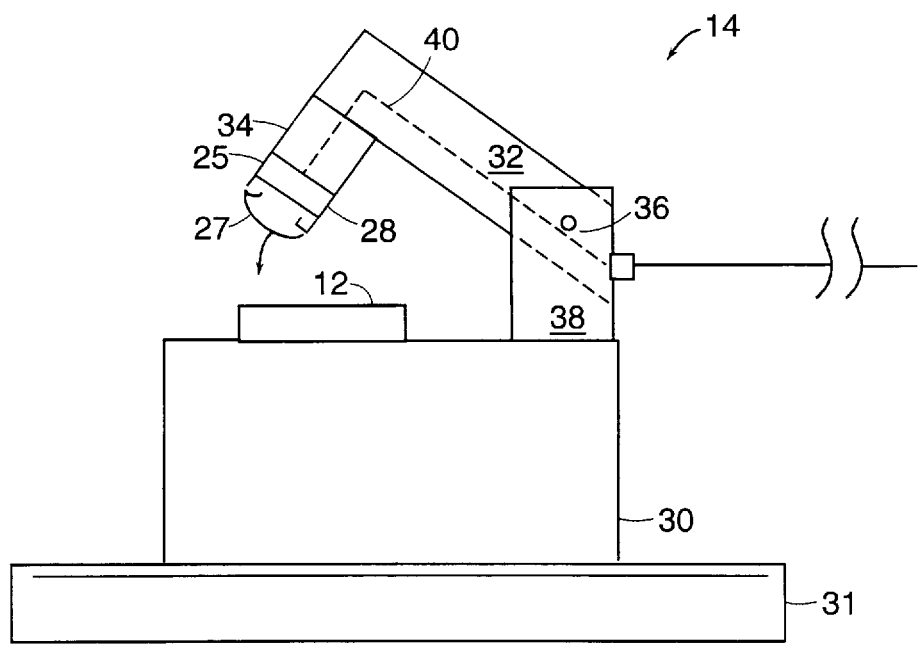

Referring now to FIGS. 8A and 8B, during the measurement process, the sample 12 is impacted with an impulsive force delivered from the force-delivering mechanism 14 in order to generate a time-dependent waveform. As is shown in FIG. 8A (and FIG. 3A), the sample 12 may be positioned in a stationary manner relative to the impact plate 29 and the load cell 28, and may then be impacted with the tip 27 attached to the impacting head 34 of the hammer 32 to generate the time-domain signal. As described above, this signal is then transferred to the force-registering mechanism along signal line 40. Alternatively, as shown in FIG. 8B, the load cell 28 may be mounted on the surface of the impacting head 34. In this case, the hammer tip 27 is attached to a tip-mounting device 25, which, in turn, is attached to the load cell 28; the tip 27 is then used to directly impact the sample to register a signal, which is then sent to the force-registering system along signal line 40 positioned within the hammer.

Figure 9:
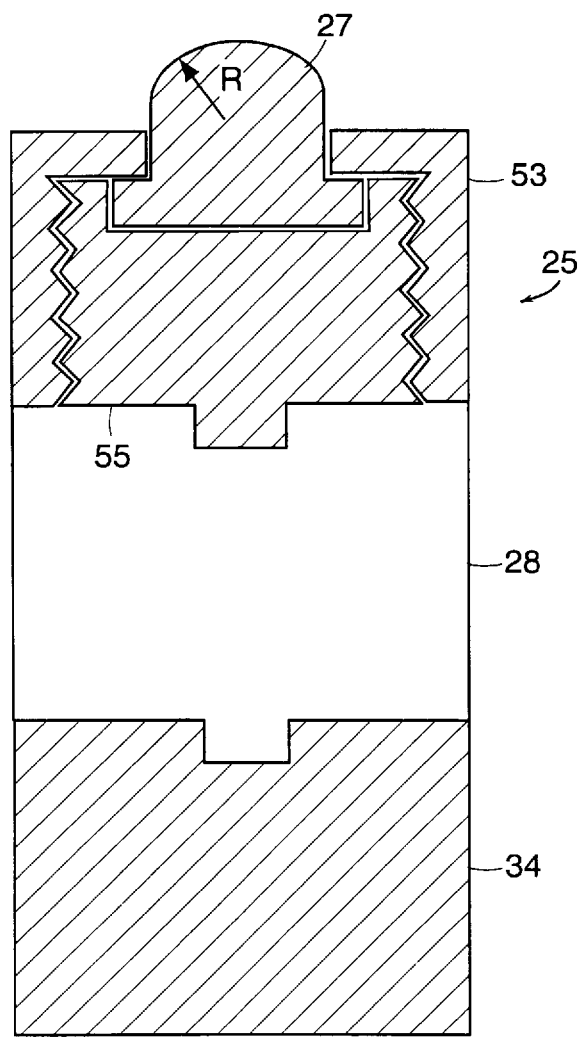
FIG. 9 is a side-sectional view of the impacting components and load cell of the force-delivering device.

Referring now to FIG. 9, different tips 27 having adjustable radii and hardnesses may be inserted into the force-delivering mechanism in order to accurately measure the SDH of the sample. In all cases, the tip 27 must have a relatively high hardness compared to the sample at the point of contact. The tip, for example, may be composed of tungsten carbide. Preferably, the tip 27 is rounded with a radius R so that an evenly distributed load can be passed from the sample onto the load cell 28. The tip can be held firmly in place with the tip-mounting device 25, which preferably includes a threaded seat 55 and cap 53. In order to effectively deliver a force to the load cell 28, these elements are attached directly to the cell and are preferably composed of materials having high stiffnesses, such as steel. Preferably, the seat 55 and cap 53 have sufficiently large sizes and masses (with respect to the tip) so that stresses and deflections will be low, thereby maximizing the accuracy of the measurement. In other embodiments, the tip 27 may screw directly into the load cell, or may be attached using alternative means. For instance, high-strength adhesives, such as epoxy, may be used. In this case, it is necessary to take the elastic properties of the adhesive into account; materials which are too soft or too brittle may fail or contribute noise to the signal during impact.

Figure 10A:
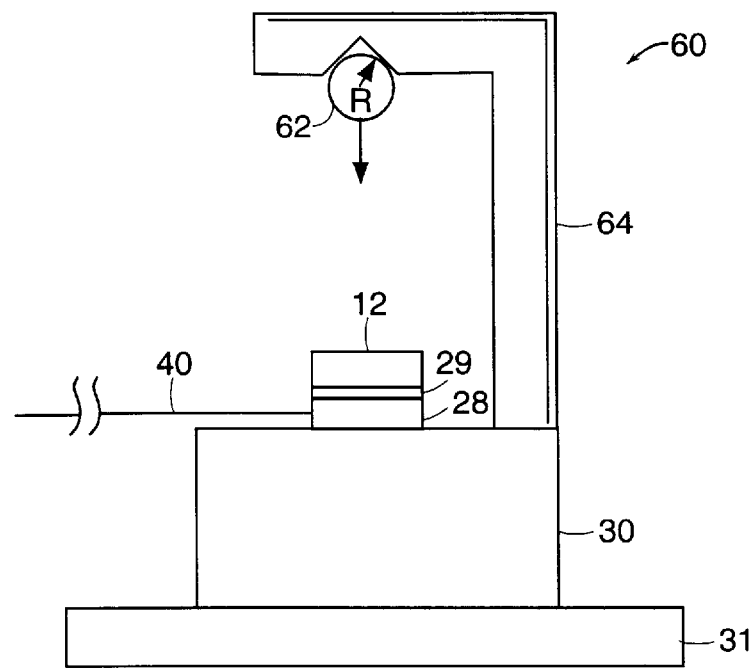
FIGS. 10A and 10B are side views of the dynamic hardness tester wherein, respectively, the force-delivering mechanism is dropped directly onto the sample, and the sample is dropped directly onto the force-delivering mechanism.
Figure 10B:
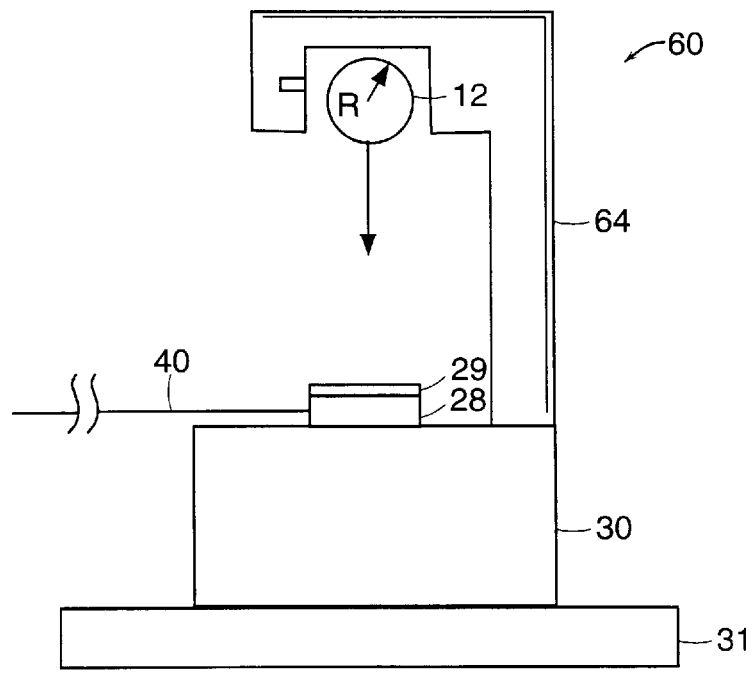
Figure 12A:
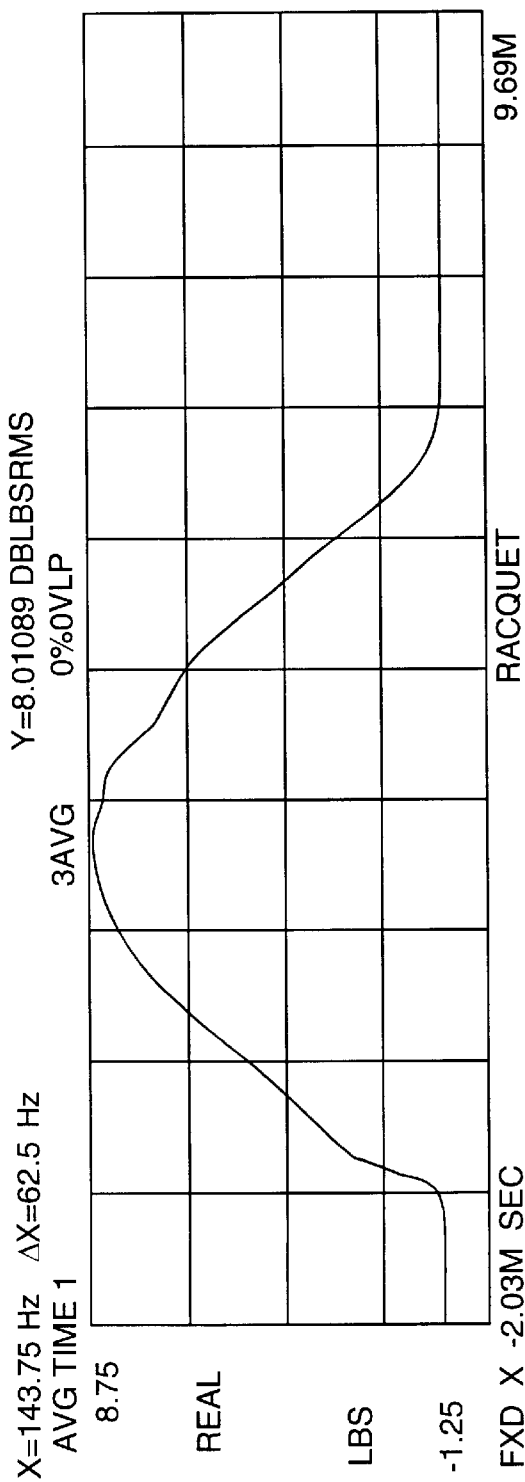
Figure 12B:
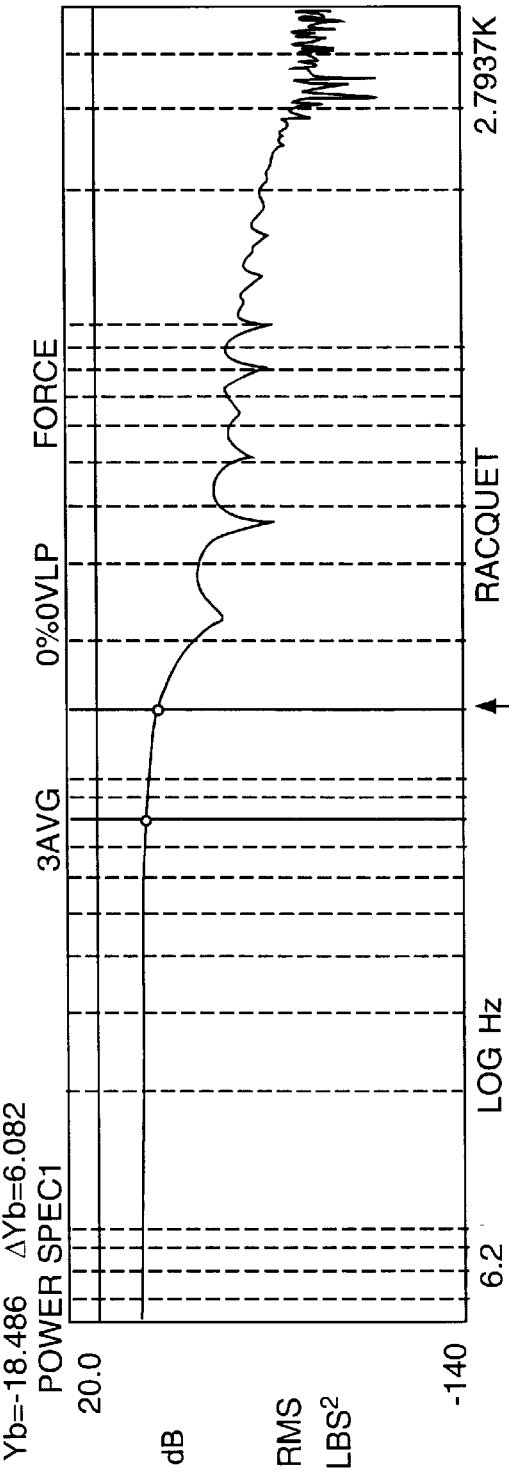
Figure 13A:
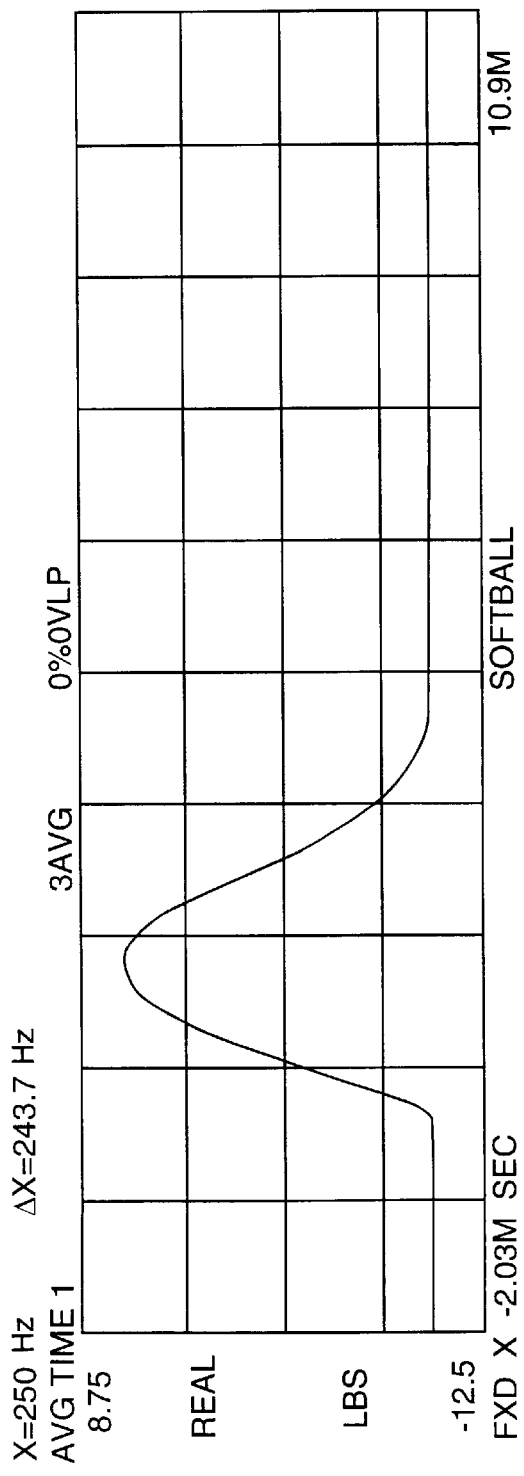
Figure 13B:
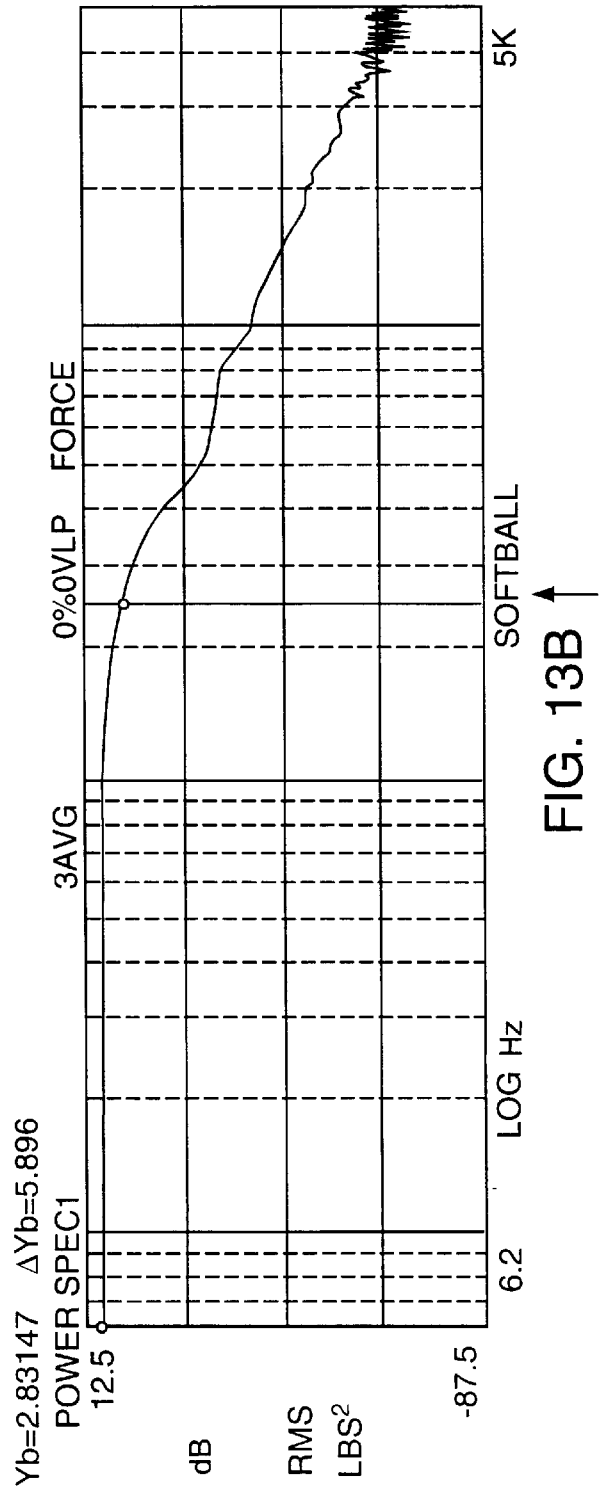
Figure 15A:
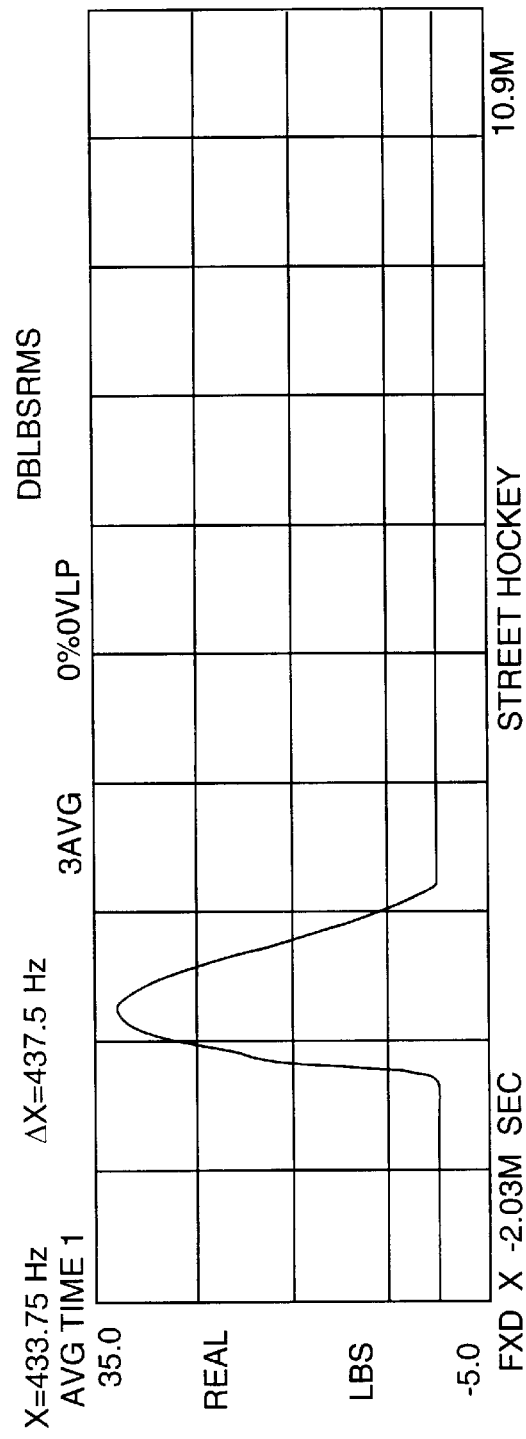
Figure 15B:
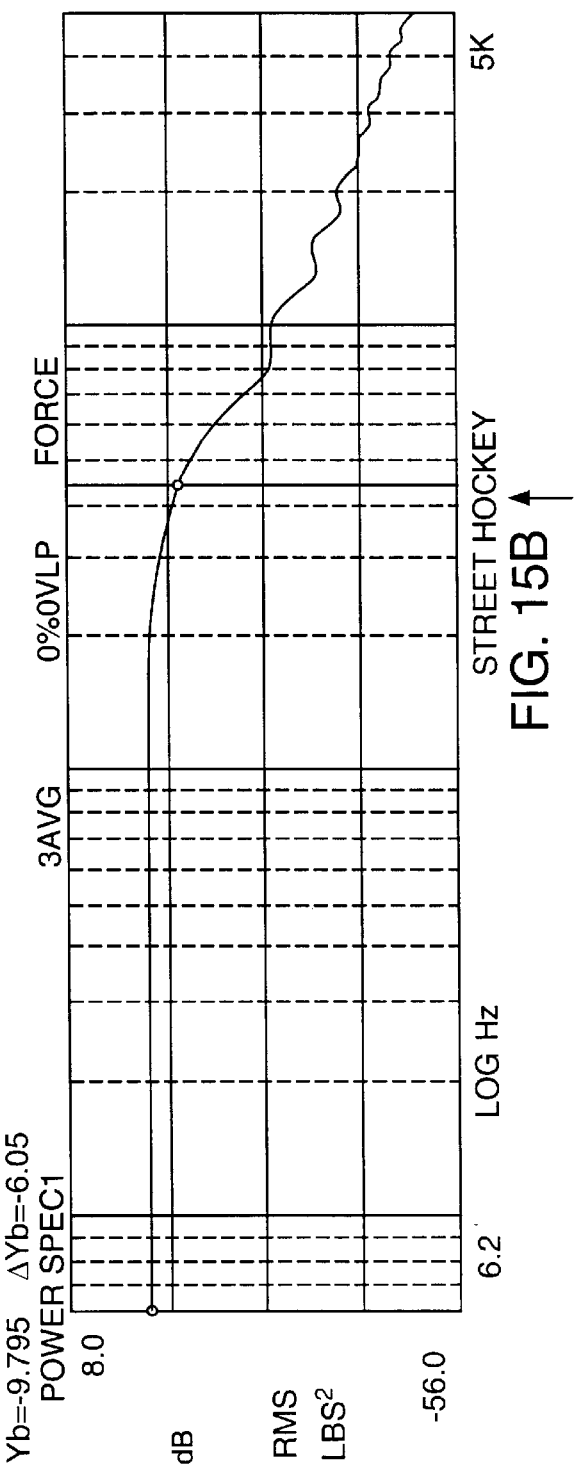

Referring now to FIG. 10A, in still other embodiments of the invention, the impulsive force provided by the force-delivering mechanism 60 may be generated by dropping a weight 62 (e.g., a steel ball having a radius R) elevated using an adjustable arm 64 onto the sample 12 mounted on top of the impact plate 29 and load cell 28. The weight may be held in place using mechanical force, or, alternatively in the case of a magnetically attracted weight, by applying a magnetic field. In either case, the magnitude of the impulse force can be easily adjusted by changing the height of the adjustable arm. Referring now to FIG. 10B, in related embodiments, the sample 12 (shown here as a ball of radius R) may be dropped directly on top of the impact plate 29 and load cell 28 in order to generate the time-dependent signal. In this case, the magnitude of the force is adjusted, as before, by changing the height of the adjustable arm 64, and the curvature of the impacting surface is provided by the curvature of the ball. In alternate embodiments, the force-delivering mechanisms shown in FIGS. 10A and 10B may employ means for propelling the steel ball or sample onto the load cell. Such propelling means include, for example, pressurized air "cannons".

In all embodiments, it is important to configure the force-delivering mechanism so that only one impact event occurs for each measured signal. Multiple impacts occurring within a single measured signal may result in erroneous determination of the SDH and the material hardness. In addition, in order to ensure accurate detection, it is preferable that when dropped the impacting ball or sample delivers an axial load near the center of the load cell. For example, if a baseball is dropped onto the side portions of the load cell, a torque may be generated, thereby reducing the accuracy of the measurement. In order to minimize the probability of such an occurrence, it is preferable that the load cell and impact plate have a relatively large cross section compared to the sample.

Different features of the embodiments shown in FIGS. 8A, 8B, 10A, and 10B can be combined or modified to form alternate force-delivering mechanisms. For example, the load cell and impact plate may be connected to the impacting end of a hand-held hammer used to generate an impulsive force; a device having this general structure is described in U.S. Pat. No. 5,079,728, the contents of which are incorporated herein by reference. In a related example, the sample may be affixed to the hammer, and used to strike the load cell in order to generate the impulsive force.

The method and apparatus described above are especially effective in determining the dynamic hardness of elastic materials, such as balls, bats, pucks, sticks, protecting devices and related equipment, such as padding and helmets, used in sports such as baseball, hockey, ping pong, and other sports. In this case, the 'sample' indicated in FIGS. 8 and 10 is the piece of sporting equipment, and measurements are carried out as described above to determine the SDH corresponding to the object being measured.

Once determined, the SDH can be used to rate and categorize the piece of equipment being tested. For example, using the measurement device shown in FIG. 10B, baseballs may be individually dropped onto the impact plate/load cell system attached to a large inertial mass. By keeping the drop height at a reasonable distance (a baseball dropped from a height of about 1 foot has an impact velocity of about 8 feet/second) balls can be tested non-destructively, allowing the SDH and DSDH to be obtained.

The SDH of a material can be used as both a diagnostic measurement tool and performance indicator. For example, the SDH values of bats and baseballs can be used to determine the ball's ability (or lack of ability) to support higher resonances, or excite higher resonances in an impacting bat. In the case of a ball, the resonance frequency of interest is the frequency of oscillation between the core of the ball (represented by mass $M_1$) and the annulus of the ball (represented by mass $M_2$). This oscillation may be excited following impact with a bat, or when the ball is propagating through the air after being thrown. Deposition of energy into the oscillatory mode may effect the ball's performance, and thus consideration of the SDH relative to the resonance frequency during design allows balls having different properties to be manufactured. For instance, in order to maximize the initial speed of the ball, $M_1$, $M_2$, and the materials used to make the ball are chosen so that the resonance frequency is above the SDH; this minimizes the vibratory motions excited between the core and annulus during impact. These motions may take energy away from the rigid-body motion of the ball. This criteria can additionally be used during manufacturing as a quality-control measure: balls having SDH values which fall below specifications (i.e., balls which are too "lively" or too "soft") may be rejected from the processing line. In addition, reduced-injury-factor ("RIF") baseballs having low SDH values (typically in the range of 170 Hz) can be designed to minimize injury following impact. In this case, $M_1$, $M_2$, and the materials used to make the ball are preferably chosen so that the SDH is above the resonance frequency of the ball.

The SDH can also be used to design protective equipment (e.g., chest protectors) which reduce the probability of injury. For example, a baseball can be designed to be compressible and have an SDH value below that of the chest protector or glove in order to reduce the chance of injury following impact.

Similarly, by changing the skin thickness or composition of a metal (e.g., aluminum) bat, the SDH value can be increased or decreased to maximize or minimize the amount of vibration in the bat due to impact. The velocity dependence of the SDH, determined by the relative velocity between the ball and bat, must be taken into account. In this case, the SDH used during design is derived from the effective spring constant $k_{eff}$ related to the spring constant of the bat ($k_{bat}$) and the ball ($k_{ball}$)

$$\frac{1}{k_{eff}} = \frac{1}{k_{ball}} + \frac{1}{k_{bat}} \quad (16)$$

By inserting $k_{eff}$ into equations (3) and (4), the SDH for the interaction can be determined, and then used as a design parameter. By keeping the bat's resonance frequency value above the effective SDH value, the number of transverse, torsional, and longitudinal modes excited in the bat following impact are minimized. This prevents a phenomenon which causes the well-known "sting" occurring when a pitched ball impacts the bat near the handle, and also increases the probability of the user generating a "clean hit". In addition, this design can be used to minimize the high-pitch "ping" sound from aluminum bats which occurs following impact. This same principal can be used during the design of other items having elongated cylindrical or rectangular portions, such as golf clubs or hockey sticks.

In other types of sports items (e.g., tennis rackets) it may be desirable to design a component of the item (e.g., the stringed racket face) to enhance the propagation of the ball after impact. For example, the stringed region may be designed so that the SDH is above the resonance frequency of the tennis ball, thereby maximizing the spring-like "trampoline" effect which effectively propels the incident ball. Moreover, in order to minimize vibrations following impact, the SDH of the composite material surrounding the racket strings may be designed to be below the resonance frequency of that material. It is desirable to minimize these vibrations, as they may propagate into the user's hands following impact to cause a stinging affect.

In another embodiment, sports items may be designed with the DSDH in mind. For example, using the spring-mass expression for DSDH shown in equation (11), the product of the DSDH and the SDH is $-\gamma=-0.7737$. Materials having an SDH-DSDH product below this value in magnitude will be damped, and show little trampoline effect, while SDH-DSDH products above this value in magnitude indicate that the material will exhibit negative damping, acoustic, or trampoline effects.

In still other embodiments, the SDH value of a ball can be evaluated and compared to SDH values of balls from previous years in order to maintain the integrity of the sport. For example, if baseballs used during a particular season have a high SDH value, these balls are expected to be more lively, and the home runs production during that season, for example, would be expected to increase. Thus, knowledge of the ball's SDH value from year to year would allow accurate comparison of players' statistics from different time periods.

The SDH value can be used as a design parameter to maximize the performance of other types of sporting equipment. For example, the projectile characteristics of golf balls can be adjusted by modifying the compression or modulus of elasticity of the club head or ball; these parameters, in turn, are dependent on the corresponding velocity-dependent SDH values. By keeping the resonance frequency of the golf club above the SDH of the ball and club head, and the SDH of the club head above the SDH of the golf ball, vibrations in the club following impact can be reduced. The properties of other sports equipment, such as ping pong, racquet, bowling, and tennis balls, hockey pucks, marbles, gloves, rackets, shin guards, and paddles can be adjusted in a similar manner with knowledge of the material SDH and DSDH.

Other materials, both elastic and non-elastic, may be tested and evaluated according to the method and apparatus of the invention. Samples containing, for example, metals, ceramics, plastics, glasses, or polymeric materials may be evaluated. For example, the method may be used to monitor the hardness of kevlar used in bullet-proof vests, or the hardness of armor used in miltary-based vehicles (e.g., tanks and helicopters). As before, the properties of these materials related to the SDH and DSDH values include, for example, the modulus of elasticity, Poisson's ratio, stiffness, and coefficient of restitution.

The following are examples of measurements of the SDH and DSDH values of various types of sports balls made using the method and apparatus of the invention.

EXAMPLES

Tests have been performed using 46 different sports balls, ranging in size from marbles to bowling balls, in order to determine their SDH values. In all cases, the dynamic hardness tester used to perform the measurements included the following equipment:

Hewlett Packard model 3562A Dynamic Signal Analyzer, Ser. No. 2435A00275; Including Hewlett Packard Dual 3.5" Disk, Drive model 9122D, Ser. No. 2518A40463 and Hewlett Packard Plotter model 7470A, Ser. No. 2308A97959.

PCB Piezotronics model 208A03 Force Transducer, Ser. No. 8331, with calibrated range of 0 to 100 pounds (purchased from PCB Piezotronics, New York).

PCB Piezotronics model 480D06 Power Unit, Ser. No. 6129.

Equipment Set-UD

The dynamic hardness tester, as shown in FIGS. 3A, included a 121.5-pound (540.4 newtons) steel block used to mount the force transducer. The mass of the steel block was chosen to be significantly larger than any of the sports balls tested to ensure that vibrations induced by the impact of the ball would be extremely small in amplitude. Attached to the face of the transducer was a flat steel impact plate.

During experiments, the signal generated by the transducer was sent along a co-axial cable connected to a PCB power unit having a gain setting of one. The output of the power unit was then sent to input channel 1 of a signal analyzer, which was connected to a dual disk drive for storage of information, and to a plotter for printing of the acquired data curves.

In order to generate data, sports balls were individually dropped from a predetermined height of about 10 inches onto the impact plate of the load cell. Balls dropped from this height had a velocity of about 7.3 ft/sec (2.23 meters/sec). Because of their weight, bowling balls were dropped from a height of a approximately 0.25 inches, while pool cue balls were dropped from a height of 2 inches. Measurement of impact velocity was made using the formula $v_0 = (2gh)^{1/2}$, and all triggering of the signal analyzer was done using a pretrigger signal.

Test Procedure

The dynamic signal analyzer used in all experiments (i.e., the HP 3562A) was set-up to allow data to be collected in the time domain, converted to the corresponding power spectra, and then analyzed to determine the −6 dB cut-off frequency.

Once the equipment was set up, a general test procedure was implemented by dropping the ball onto the impact plate of the load cell. The START key on the HP 3562A signal analyzer 40 was pushed. This armed the HP 3562A trigger and allowed a reading to occur when the input to channel 1 from the load cell reached a certain voltage (approximately 80 millivolts). The ball was then dropped so that it impacted the load cell impact plate; following impact, the pretrigger signal was generated and sent to the HP 3562A to allow recording of the force-versus-time record and the power spectrum for the impact. The process was repeated until four consistently timed sets of data were accumulated and averaged together by the HP 3562A for the selected ball. The time-dependent waveform and power spectrum were then stored on a 3.5-inch floppy disc.

Time and frequency-dependent data taken from tennis ball, racquet ball, softball, baseball, hockey puck, and golf ball samples are shown, respectively, in FIGS. 11A–16A, and 11B–16B. Time dependencies of the material response were measured according to the invention; following transformation into the frequency domain, the data were examined to determine the SDH value (i.e., the −6 dB cut-off frequency indicated in each figure by the arrow).

The frequency-domain data are shown using a logarithmic scale for the frequency axis (x axis); this allows emphasis of low-frequency components. During analysis, the peak value of each power spectrum was determined using the "MRKR PEAK" soft key accessed through the "SPCL MARKER" hard key from the "MARKER" key group. After the peak value of the power spectrum was found, the cut-off frequency (in Hertz) was determined by moving one cursor to the frequency corresponding to $f_{-6\ dB}$ relative to the zero-frequency amplitude. This frequency, shown for each trace as the "x" value in the upper-left-hand corner, is the SDH for the measured material. The $\Delta x$ value for each trace refers to the difference in frequencies between $f_{max}$ and $f_{-6\ dB}$. As discussed above, in general, the time-domain response for each sample had a gaussian shape corresponding to the time period when the ball and impact plate where in contact with each other. The rates of incline and decline of the rising and falling edges of each data scan were directly related to the determined SDH value; higher frequencies resulted from waveforms having rising (falling) edges with faster rates of incline (decline).

From the data shown in the figures, it is clear that the tennis ball sample (Penn, Inc.) had one of the lowest SDH value (112.5 Hz) while the golf ball (MaxFli) had one of the highest values (1094 Hz). The lowest SDH value was measured in the RIF baseball (75 Hz), while the highest value was measured in a glass marble (23.6 kHz). These data are consistent with the analysis provided above: soft, compressible tennis balls maintain contact with the impacting surface for time periods (in this case, about 4 milliseconds) substantially longer than the relatively stiff golf ball (a few hundred microseconds) having a similar weight. The results (e.g., SDH, DSDH, impact velocity, weight, and impact force) for all 46 balls are listed in Table 3, below. In particular, the table includes three columns for the DSDH of each material. The original DSDH, defined above as the slope at the SDH value, was originally measured for the log-log plots, and is listed in units of dB/decade. The DSDH was then remeasured for a linear power spectrum-vs.-frequency plot, and is listed in the adjacent column in units of $lbs^2/Hz$. This value was then normalized for the peak power spectrum amplitude (having units of $lbs^2$), and is listed in the adjacent column of the table as having units of 1/Hz. The final column under the DSDH heading lists the DSDH multiplied by the SDH; this value is dimensionless and of negative sign.

In a separate set of experiments, the SDH, Rockwell E hardness, and wear-resistance values of electron-irradiated PTFE polymers were measured and compared. In this experiment, electron radiation causes the polymer to cure, and thus higher dosages of radiation results in the formation of a harder polymer.

The SDH for each sample was measured using an apparatus similar to that shown in FIG. 10A. A 0.25-inch diameter steel ball was dropped on the polymer sample from a height of 2 inches, resulting in a final impact velocity of 39.3 inches/second. Following impact, the resulting time and frequency-domain responses were determined as described herein. After the SDH of each sample was measured, the Rockwell E hardness and wear-resistance values were determined independently using experiments performed by T. Blanchet and Y. Peng carried out on standard testing devices (private communication). The results for the samples are shown in Table 4, below.

TABLE 4

| Comparison of SDR and Conventional Hardness Measurements | | | |
|---|---|---|---|
| Radiation Dosage (arb.) | SDH (kHz) | Rockwell Hardness (arb.) | Relative Wear Resistance |
| 0 | 3.838 | 42.8 | 1 |
| 2 | 3.875 | 44.3 | 4 |
| 5 | 3.937 | 46.3 | 225 |
| 10 | 3.963 | 47.0 | 523 |
| 20 | 4.050 | 48.3 | 928 |
| 30 | 4.275 | 52.4 | 1180–2339 |

As is clear from the table, the polymers' SDH values increase along with conventional hardness indicators as the degree of curing, and corresponding hardness values, of the samples increase.

TABLE 3

Hardness of Various Sports Balls

| Number | | | | Mass | | | DSDH | | | Peak Force | | Incident Velocity | | (SDH) | Relative Hardness |
|---|---|---|---|---|---|---|---|---|---|---|---|---|---|---|---|
| N | Ball Type | Manufacturer | SDS Hz | g | -dB/dec | $-10^{-3}\text{Lb}^2/\text{Hz}$ | $-10^{-3}/\text{Hz}$ | Hz | (*-1) | lb | ft/s | m/s | $\times \text{ m}^{1/2}$ $g^{1/2}\text{ Hz}$ | (S1/S0) $[(\text{m1/m0})]^{-1}$ |
| 1 | Base, RIF 1 | Worth | 75 | 146.7 | 30.087 | 60.2500 | 10.120 | 0.759 | 21 | 7.3 | 2.23 | 908 | 0.164027 |
| 2 | Base, Tee | Rawlings | 81 | 138.5 | 27.974 | 49.1530 | 9.450 | 0.767 | 22 | 7.3 | 2.23 | 956 | 0.172127 |
| 3 | Tennis | Penn | 113 | 56.8 | 29.822 | 5.3460 | 6.906 | 0.777 | 12 | 7.3 | 2.23 | 848 | 0.904797 |
| 4 | Racquet | Unknown | 125 | 40.5 | 31.816 | 0.6179 | 6.117 | 0.765 | 8.7 | 7.3 | 2.23 | 795 | 1.00000 |
| 5 | Tennis | Wilson | 125 | 56.7 | 28.420 | 4.8623 | 6.156 | 0.770 | 13 | 7.3 | 2.23 | 941 | 1.00000 |
| 6 | Base, RIF 5 | Worth | 169 | 147.5 | 30.116 | 21.4290 | 4.355 | 0.735 | 43 | 7.3 | 2.23 | 2049 | 0.370614 |
| 7 | Lacrosse | Unknown | 181 | 154.2 | 29.575 | 5.3343 | 4.212 | 0.763 | 47 | 7.3 | 2.23 | 2250 | |
| 8 | Handball, brite blue, red dot | Spalding | 188 | 64.4 | 29.822 | 5.2277 | 4.159 | 0.780 | 23.5 | 7.3 | 2.23 | 1505 | |
| 9 | Squash, Yellow dot | Dunlop | 200 | 24.5 | 30.383 | 0.4252 | 3.701 | 0.740 | 7.6 | 7.3 | 2.23 | 990 | 0.361415 |
| 10 | Base, Pitching Machine | DeBeers | 219 | 140.4 | 30.196 | 17.0090 | 3.425 | 0.749 | 55 | 7.3 | 2.23 | 2591 | 0.468562 |
| 11 | Soft | Unknown | 250 | 197.8 | 28.420 | 20.8450 | 2.926 | 0.732 | 78 | 7.3 | 2.23 | 3516 | 0.558843 |
| 12 | Bowling, 300, (12.5 pound) | High Skore, Japan | 288 | 5670 | 34.355 | 15.0320 | 3.004 | 0.864 | 68.8 | 1.2 | 0.4 | 21649 | 0.885213 |
| 13 | Bowling, 300, (10 pound) | Galaxy | 363 | 4564 | 33.063 | 8.3113 | 2.343 | 0.849 | 76.6 | 1.2 | 0.4 | 24490 | 1.000000 |
| 14 | Base, National League | Rawlings | 400 | 150.6 | 27.697 | 7.2179 | 1.766 | 0.706 | 98 | 7.3 | 2.23 | 4909 | 0.886363 |
| 15 | Ice Hockey Puck | In Glas | 400 | 163 | 28.780 | 4.8590 | 1.801 | 0.720 | 77 | 7.3 | 2.23 | 5107 | |
| 16 | Soft, Red dot | Worth | 406 | 183 | 29.525 | 12.5680 | 1.859 | 0.755 | 120 | 7.3 | 2.23 | 5495 | 0.872479 |
| 17 | Base, Babe Ruth | Rawlings | 438 | 144.7 | 28.169 | 6.3307 | 1.605 | 0.702 | 105 | 7.3 | 2.23 | 5263 | 0.951366 |
| 18 | Street Hockey Puck | Cooper | 444 | 57.9 | 30.537 | 0.7226 | 1.712 | 0.759 | 33 | 7.3 | 2.23 | 3376 | |
| 19 | Soft, Blue Heat | Dudley | 444 | 182.2 | 26.727 | 10.3630 | 1.535 | 0.681 | 135 | 7.3 | 2.23 | 5989 | 0.952052 |
| 20 | Superball | Unknown | 456 | 8.7 | 30.690 | 0.0385 | 1.655 | 0.755 | 7.9 | 7.3 | 2.23 | 1346 | 0.952052 |
| 21 | Base, Little League | Rawlings | 458 | 147.5 | 28.432 | 6.3742 | 1.546 | 0.705 | 110 | 7.3 | 2.23 | 5541 | 1.000000 |
| 22 | Soft, Blue dot | Worth | 463 | 180.5 | 29.814 | 9.3927 | 1.608 | 0.743 | 126 | 7.3 | 2.23 | 6214 | 0.986016 |
| 23 | Soft, Green dot | Worth | 488 | 166.4 | 29.431 | 9.5754 | 1.504 | 0.733 | 140 | 7.3 | 2.23 | 6289 | 1.000000 |
| 24 | Golf, EAR | Cabot Corp. | 519 | 52.7 | 28.289 | 0.0734 | 1.364 | 0.707 | 28 | 7.3 | 2.23 | 3765 | 0.466389 |
| 25 | Cricket | Unknown | 538 | 157.4 | 27.841 | 6.8257 | 1.309 | 0.704 | 159 | 7.3 | 2.23 | 6743 | |
| 26 | Squash, Orange dot | Slazenger | 550 | 21.8 | 29.000 | 0.1302 | 1.345 | 0.740 | 19.6 | 7.3 | 2.23 | 2568 | 0.937527 |
| 27 | Badminton, Shuttlecock | Wilson | 550 | 5.3 | 29.600 | 0.0074 | 1.375 | 0.756 | 4.7 | 7.3 | 2.23 | 1266 | |
| 28 | Squash, Blue dot | Merco-West | 563 | 20.4 | 30.400 | 0.1082 | 1.346 | 0.757 | 18 | 7.3 | 2.23 | 2541 | 0.926711 |
| 29 | Field Hockey | Cran Barry | 575 | 154.1 | 29.700 | 7.1208 | 1.316 | 0.757 | 152 | 7.3 | 2.23 | 7138 | |
| 30 | Squash, White dot | Slazenger | 588 | 21.7 | 28.800 | 0.1168 | 1.231 | 0.723 | 20.5 | 7.3 | 2.23 | 2737 | 1.000000 |
| 31 | Golf, Wiffle | Unknown | 625 | 5.1 | 28.600 | 0.0003 | 1.138 | 0.711 | 1.4 | 7.3 | 2.23 | 1411 | 0.175057 |
| 32 | Golf, Glow | Unknown | 806 | 44.1 | 29.685 | 0.3797 | 0.920 | 0.742 | 64 | 7.3 | 2.23 | 5354 | 0.684437 |
| 33 | Golf, Titleist DT-80 | Titleist | 1019 | 45.8 | 30.014 | 0.4899 | 0.744 | 0.758 | 95 | 7.3 | 2.23 | 6894 | 0.855303 |
| 34 | Golf, ZLS-100 | Hogan | 1069 | 45.9 | 29.344 | 0.4501 | 0.695 | 0.743 | 100 | 7.3 | 2.23 | 7240 | 0.897410 |
| 35 | Golf, CD-100 | MaxFli | 1088 | 45.7 | 28.867 | 0.3999 | 0.671 | 0.730 | 97 | 7.3 | 2.23 | 7352 | 0.917252 |
| 36 | Golf, HT-100 | MaxFli | 1100 | 44.8 | 29.443 | 0.39Q1 | 0.678 | 0.745 | 97 | 7.3 | 2.23 | 7363 | 0.913156 |
| 37 | Golf, DDH-90 | MaxFli | 1144 | 45.7 | 30.580 | 0.3983 | 0.673 | 0.770 | 102 | 7.3 | 2.23 | 7732 | 0.959174 |
| 38 | Ping Pong, 3 star yellow | Player's Edge | 1194 | 2.81 | 37.700 | 0.0018 | 0.789 | 0.942 | 6.1 | 7.3 | 2.23 | 2001 | 0.920100 |
| 39 | Golf, MD-100 | MaxFli | 1194 | 45.6 | 29.030 | 0.4122 | 0.614 | 0.733 | 110 | 7.3 | 2.23 | 8061 | 1.000000 |

TABLE 3-continued

Hardness of Various Sports Balls

| Number N | Ball Type | Manufacturer | SDS Hz | Mass g | DSDH -dB/dec | DSDH $-10^{-3} Lb^2/Hz$ | DSDH $-10^{-3}/$ Hz | DSDH (*-1) | Peak Force lb | Incident Velocity ft/s | Incident Velocity m/s | (SDH) $\times m^{1/2}$ $g^{1/2} Hz$ | Relative Hardness (S1/S0) $[(m1/m0)]^{-1}$ |
|---|---|---|---|---|---|---|---|---|---|---|---|---|---|
| 40 | Bocce, Wood comp., Acrylic finish | Forster | 1263 | 451.9 | 31.600 | 3.6278 | 0.633 | 0.799 | 343 | 2.3 | 0.70 | 26828 | |
| 41 | Ping Pong | Sportcraft | 1263 | 2.81 | 38.103 | 0.0017 | 0.762 | 0.963 | 6.5 | 7.3 | 2.23 | 2116 | 0.954007 |
| 42 | Croquet | Unknown | 1275 | 170.4 | 31.500 | 0.0255 | 0.618 | 0.788 | 28 | 5.2 | 1.6 | 16644 | |
| 43 | Ping Pong, 3 star white | Halex | 1288 | 2.81 | 32.100 | 0.0012 | 0.628 | 0.809 | 6.2 | 7.3 | 2.23 | 2158 | 0.9917660 |
| 44 | Ping Pong, 3 star orange | Butterfly | 1300 | 2.8 | 35.000 | 0.0014 | 0.676 | 0.878 | 6.4 | 7.3 | 2.23 | 2175 | 1.000000 |
| 45 | Pool Cue Ball | Player's Edge | 2256 | 162 | 32.800 | 0.3180 | 0.366 | 0.825 | 242 | 3.3 | 1.01 | 28717 | |
| 46 | Marble, plastic | Unknown | 11687 | 1.82 | 30.478 | 0.0304 | 0.661 | 0.772 | 28 | 7.3 | 2.23 | 15757 | 0.3293930 |
| 47 | Marble, glass | Unknown | 23625 | 4.1 | | | | | 227 | 7.3 | 2.23 | 47837 | 1.0000000 |

Other embodiments are within the scope of the following claims.

What is claimed is:

1. A method for determining the degree of dynamic hardness of a material, said method comprising:

impulsively exciting a surface of the material by impacting the surface against a second, relatively hard surface, said second surface being in contact with a force-measuring device, measuring a signal from the force-measuring device to determine a frequency-dependent spectrum of the force exerted by the excited surface on the second surface during a time period wherein the surfaces are in direct contact, determining a roll-off frequency of the frequency-dependent spectrum, and analyzing the roll-off frequency to determine the degree of dynamic hardness of the material.

2. The method of claim 1, further including measuring the time dependence of the force exerted by the impulsively excited surface on the second surface during the time period wherein the surfaces are in direct contact.

3. The method of claim 2, wherein the measured time-dependent force is processed with a Fourier transforming algorithm to generate the frequency-dependent spectrum.

4. The method of claim 3, wherein the frequency-dependent spectrum is a power spectrum.

5. The method of claim 1, wherein the roll-off frequency corresponds to a region of the frequency-dependent spectrum wherein the intensity of the region is attenuated from the maximum value of the spectrum by a predetermined amount.

6. The method of claim 5, wherein the predetermined amount is between −2 dB and −8 dB.

7. The method of claim 6, wherein the predetermined amount is about −6 dB.

8. The method of claim 5, wherein in order to determine the dynamic hardness of the material, said analyzing further includes comparing the determined roll-off frequency of the frequency-dependent spectrum for the material against a predetermined range of roll-off frequencies of frequency-dependent spectra for materials having known dynamic hardnesses.

9. The method of claim 1, wherein said method further includes establishing a predetermined range of acceptable impact velocities between the material and the second surface, measuring the relative impact velocity between the material and the second surface, and, considering only data for instances when the measured impact velocity is within the predetermined range when determining the roll-off frequency of the frequency-dependent spectrum for the material.

10. The method of claim 1, wherein the material comprises metals, ceramics, plastics, glasses, or polymers.

11. A method for determining the degree of dynamic hardness of a material, said method comprising:

impulsively exciting a surface of the material by impacting the surface against a second, relatively hard surface, said second surface being in contact with a force-measuring device, measuring a signal from the force-measuring device to determine a frequency-dependent spectrum of the force exerted by the excited surface on the second surface during a time period wherein the surfaces are in direct contact, determining a roll-off frequency of the frequency-dependent spectrum, and analyzing the roll-off frequency to determine the degree of dynamic hardness of the material, the material being a sporting equipment item comprising one or more of metals, ceramics, plastics, glasses, and polymers.

12. A method for determining the vibratory response of a material, said method comprising:

measuring the dynamic hardness of the material, said measuring comprising impulsively exciting a surface of the material by impacting the surface against a second, relatively hard surface, said second surface being in contact with a force-measuring device, measuring a signal from the force-measuring device to determine a frequency-dependent spectrum of the force exerted by the excited surface on the second surface during a time period wherein the surfaces are in direct contact, and determining a roll-off frequency of the frequency-dependent spectrum, and comparing the roll-off frequency of the material to a resonance frequency of the material, said comparing allowing determination of the material's vibratory response.

13. The method of claim 12, wherein during said comparing, a relatively low roll-off frequency with respect to the resonance frequency of the material indicates that said material will exhibit a reduced vibratory response following an impacting event.

14. A method for determining the vibratory response of a material, said method comprising:

measuring the dynamic hardness of the material, said measuring comprising impulsively exciting a surface of the material by impacting the surface against a second, relatively hard surface, said second surface being in contact with a force-measuring device, measuring a signal from the force-measuring device to determine a frequency-dependent spectrum of the force exerted by the excited surface on the second surface during a time period wherein the surfaces are in direct contact, and determining a roll-off frequency of the frequency-dependent spectrum, and comparing the roll-off frequency of the material to a resonance frequency of the material, said comparing allowing determination of the material's vibratory response, wherein during said comparing, a relatively low roll-off frequency with respect to the resonance frequency of the material indicates that said material will exhibit a reduced vibratory response following an impacting event, said material being a sporting equipment item.

15. A method for determining the performance of a sporting equipment item, said method comprising:

determining the vibratory response of the item by measuring its dynamic hardness, said measuring comprising impulsively exciting a surface of the item by impacting the surface against a second, relatively hard surface, said second surface being in contact with a force-measuring device, measuring a signal from the force-measuring device to determine a frequency-dependent spectrum of the force exerted by the excited surface on the second surface during a time period wherein the surfaces are in direct contact, and determining a roll-off frequency of the frequency-dependent spectrum, comparing the roll-off frequency of the item to a resonance frequency of the item, said comparing allowing determination of the item's vibratory response, and evaluating the vibratory response to determine the performance of the sporting equipment item.

16. The method of claim 15, wherein during said comparing, a relatively low roll-off frequency with respect to the resonance frequency of the sporting equipment item indicates that said item will exhibit a reduced vibratory response following an impacting event.

17. The method of claim 15, wherein said sporting equipment item is a golf club, baseball bat, or hockey stick.

18. An apparatus for determining the degree of dynamic hardness of a material, said apparatus comprising:

means for impulsively exciting a surface of the material by impacting the surface against a second, relatively hard surface, a force-measuring device, in contact with said second surface, for generating a time-dependent signal indicating the force exerted by the excited surface on the second surface during a time period wherein the surfaces are in direct contact, a force-registering device, in electrical contact with said force-measuring device, comprising means for converting the time-dependent signal into a frequency-dependent spectrum, and means for analyzing the frequency-dependent spectrum to determine a roll-off frequency indicating the degree of dynamic hardness of the material.

19. The apparatus of claim 18, wherein said force-measuring device is a load cell, a transducer, a strain gauge, a quartz crystal, or a piezoelectric-based device.

20. The apparatus of claim 18, wherein said force-registering device is a digital storage device.

21. The apparatus of claim 20, wherein said digital storage device is an oscilloscope.

22. The apparatus of claim 20, wherein said means for converting the time-dependent signal into a frequency-dependent spectrum is a Fourier transforming algorithm.

23. The apparatus of claim 18, wherein said relatively hard second surface is a metal plate.

24. An apparatus for determining the decree of dynamic hardness of a material, said apparatus comprising:

means for impulsively exciting a surface of the material by impacting the surface against a second, relatively hard surface, said second, relatively hard surface being a metal plate, said metal plate being contoured to match a shape of the surface of the material, a force-measuring device, in contact with said second surface, for generating a time-dependent signal indicating the force exerted by the excited surface on the second surface during a time period wherein the surfaces are in direct contact, a force-registering device, in electrical contact with said force-measuring device, comprising means for converting the time-dependent signal into a frequency-dependent spectrum, and means for analyzing the frequency-dependent spectrum to determine a roll-off frequency indicating the degree of dynamic hardness of the material.

* * * * *